(12) United States Patent
Yang et al.

(10) Patent No.: US 9,932,609 B2
(45) Date of Patent: Apr. 3, 2018

(54) RECOMBINANT MICROORGANISM HAVING ENHANCED 1,3-PROPANEDIOL PRODUCING ABILITY AND METHOD FOR PRODUCING 1,3-PROPANEDIOL USING THE SAME

(71) Applicant: GS CALTEX CORPORATION, Seoul (KR)

(72) Inventors: Taek-Ho Yang, Daejeon (KR); Chelladural Rathnasi, Daejeon (KR)

(73) Assignee: GS CALTEX CORPORATION, Seoul (KR)

( * ) Notice: Subject to any disclaimer, the term of this patent is extended or adjusted under 35 U.S.C. 154(b) by 0 days.

(21) Appl. No.: 15/104,979

(22) PCT Filed: Dec. 16, 2014

(86) PCT No.: PCT/KR2014/012429
§ 371 (c)(1),
(2) Date: Jun. 16, 2016

(87) PCT Pub. No.: WO2015/093832
PCT Pub. Date: Jun. 25, 2015

(65) Prior Publication Data
US 2016/0319308 A1    Nov. 3, 2016

(30) Foreign Application Priority Data
Dec. 16, 2013  (KR) .................. 10-2013-0156803

(51) Int. Cl.
*C12P 7/18*    (2006.01)
*C12N 9/10*    (2006.01)
*C12N 9/04*    (2006.01)
*C12N 9/88*    (2006.01)

(52) U.S. Cl.
CPC .............. *C12P 7/18* (2013.01); *C12N 9/0006* (2013.01); *C12N 9/1022* (2013.01); *C12N 9/88* (2013.01); *C12Y 101/01004* (2013.01); *C12Y 101/01304* (2013.01); *C12Y 202/01006* (2013.01); *C12Y 401/01005* (2013.01)

(58) Field of Classification Search
None
See application file for complete search history.

(56) References Cited

U.S. PATENT DOCUMENTS 8,455,224 B2    6/2013    Paul

FOREIGN PATENT DOCUMENTS

| | | | |
|---|---|---|---|
| CN | 102952826 | * | 3/2013 |
| CN | 103305543 | * | 9/2013 |
| EP | 2400027 A1 | | 12/2011 |
| KR | 1020040048620 A | | 6/2004 |
| KR | 1020100063585 A | | 6/2010 |
| WO | 2001012833 A2 | | 2/2001 |

OTHER PUBLICATIONS

Kumar et al. Bioresour Technol. May 2013;135:555-63. Epub Nov. 15, 2012.*
Huang et al. Bioresour Technol. Jan. 2013;128:505-12. Epub Nov. 8, 2012.*
Kizer et al. Appl Environ Microbiol. May 2008;74(10):3229-41.*
Prather et al. Curr Opin Biotechnol. Oct. 2008;19(5):468-74.*
Zhe Wu et al., Improved 1,3-propanediol production by engineering the 2,3-butanediol and formic acid pathways in integrative recombinant Klebsiella pneumonia, Journal of Biotechnology, May 9, 2013, vol. 168, 8 pages.
Jong Myoung Park et al., Genome-scale reconstruction and in silico analysis of Klebsiella oxytoca for 2,3-butanediol production, Microbial Cell Factories, 2013, vol. 12:20, 11pages.
Guang Yang, Fermentation of 1,3-propanediol by a lactate deficient mutant of Klebsiella oxytoca under microaerobic conditions, Appl Microbiol Biotechnol, Sep. 8, 2006, 8 pages.
KSBB, Abstracts of Current Biotechnology and Bioengineering(XXXII), Oct. 2013, OP18, 1 page.
International Search Report dated Mar. 6, 2015 corresponding to International Application PCT/KR2014/012429.

* cited by examiner

*Primary Examiner* — Christian Fronda
(74) *Attorney, Agent, or Firm* — Hauptman Ham, LLP

(57) ABSTRACT

The present invention relates to a recombinant microorganism for producing 1,3-propanediol, wherein a pathway converting pyruvate into 2,3-butanediol is inhibited in a microorganism having a pyruvate and acetyl CoA biosynthetic pathway. In addition, the present invention relates to a method for producing 1,3-propanediol by using the recombinant microorganism.

9 Claims, 6 Drawing Sheets

[FIG. 1]
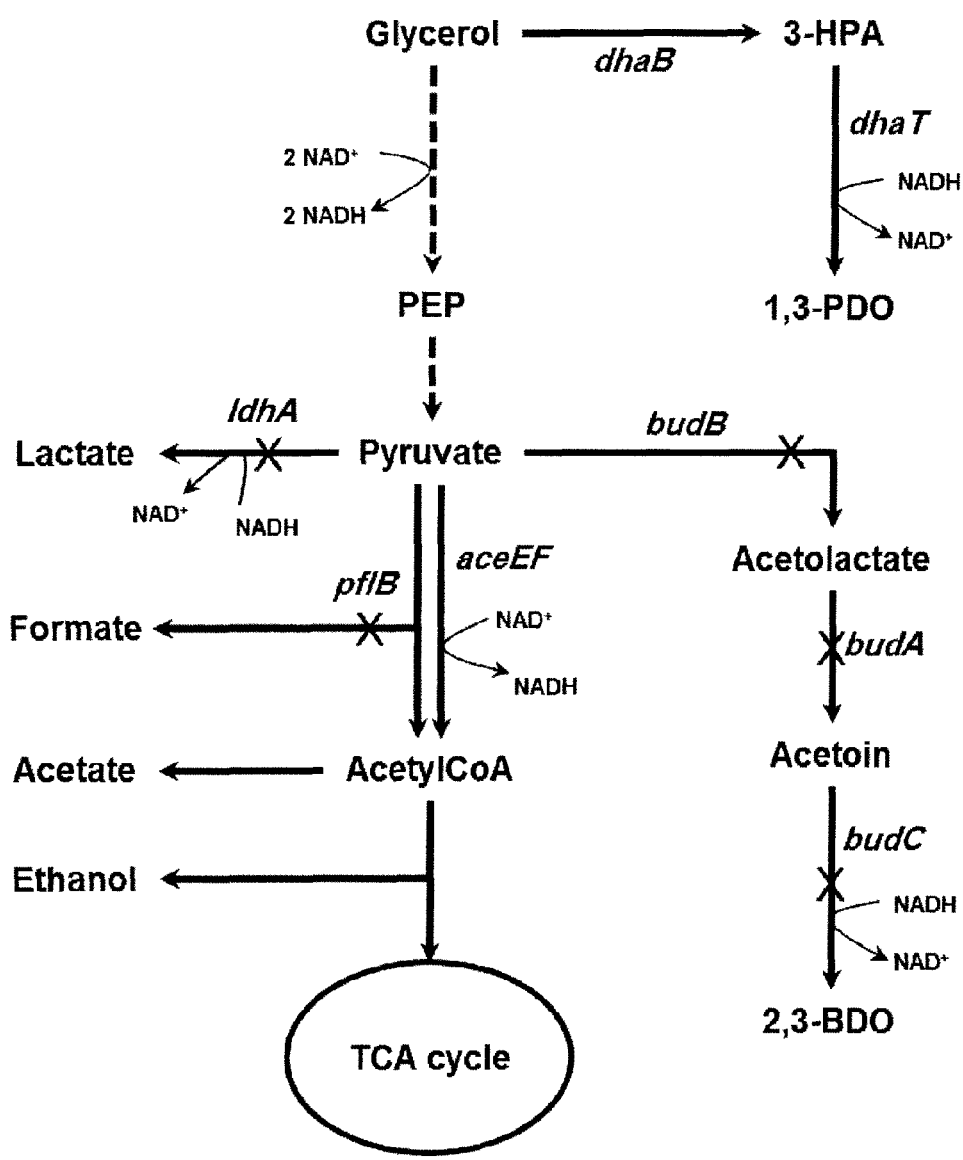

[ FIG. 2 ]
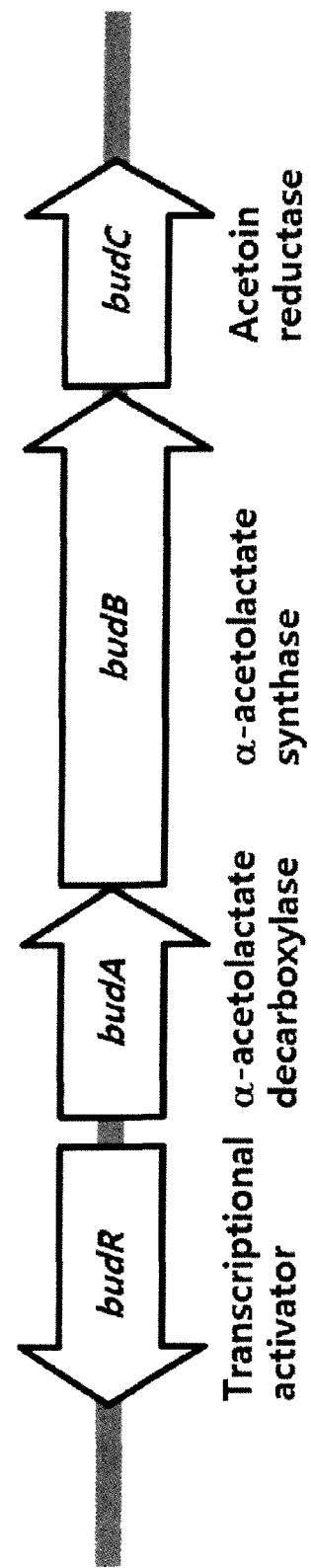

[FIG. 3]
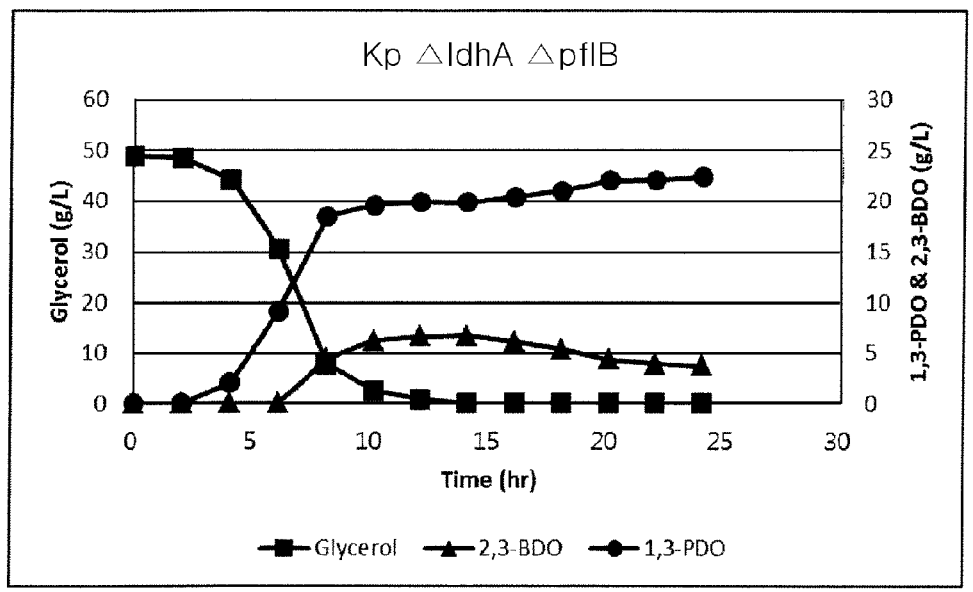

[FIG. 4]
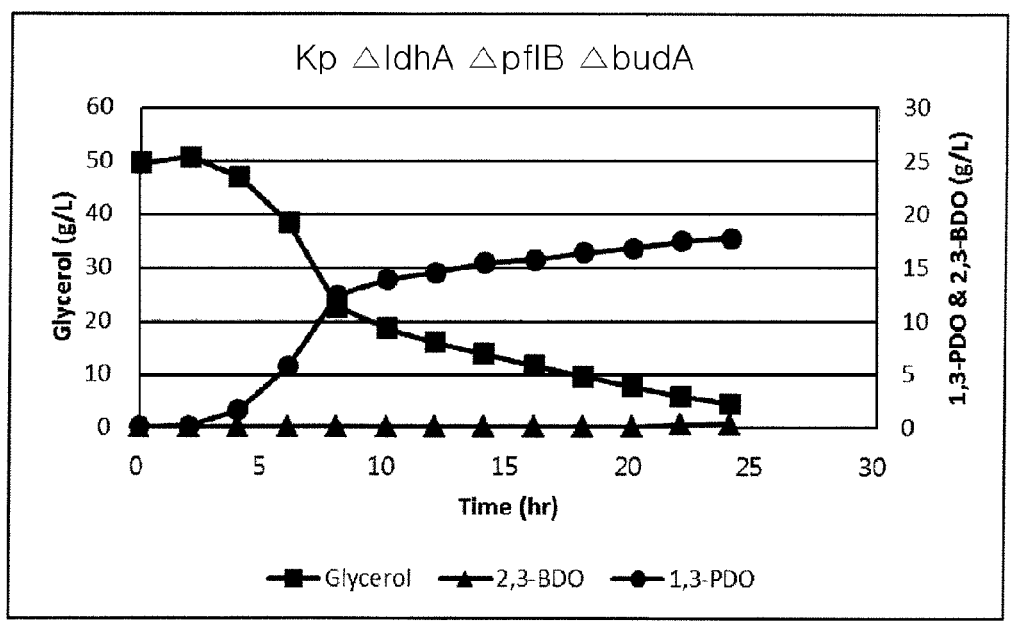

[FIG. 5]
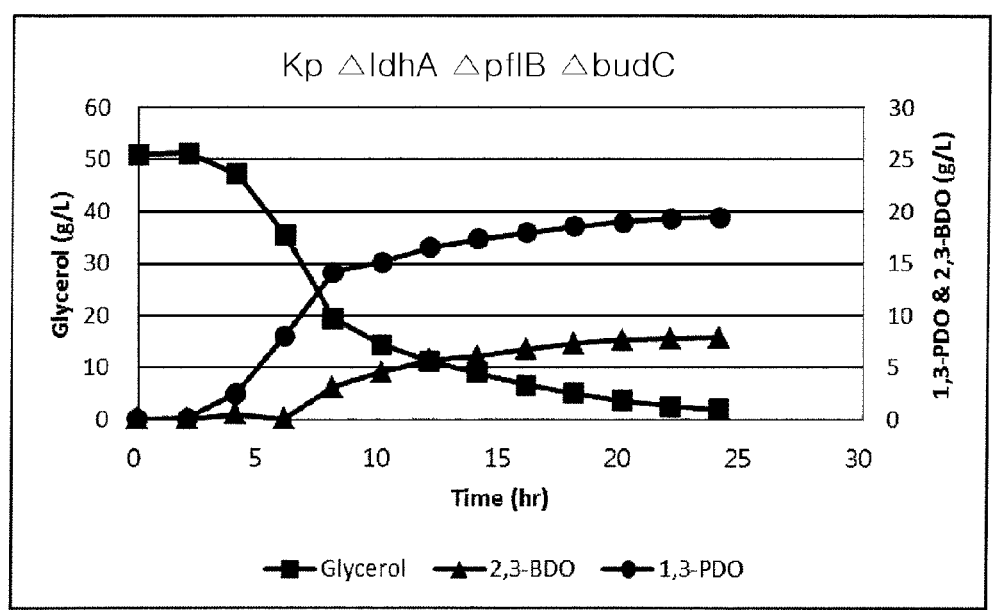

[FIG. 6]
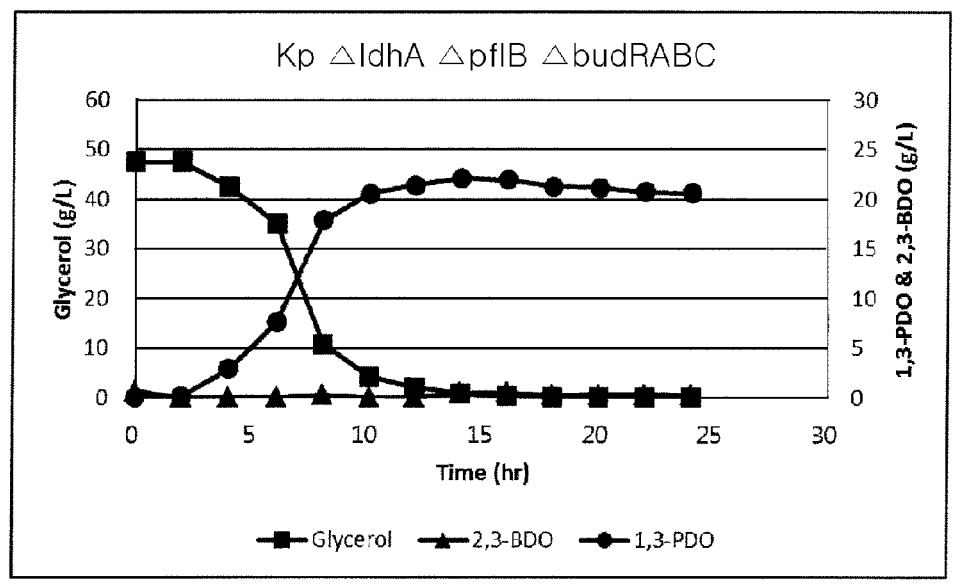

RECOMBINANT MICROORGANISM HAVING ENHANCED 1,3-PROPANEDIOL PRODUCING ABILITY AND METHOD FOR PRODUCING 1,3-PROPANEDIOL USING THE SAME

CROSS REFERENCE TO RELATED APPLICATION

This application claims the priority of Korean Patent Application No. 10-2013-0156803, filed on Dec. 16, 2013 in the KIPO (Korean Intellectual Property Office). Further, this application is the National Phase application of International Application No. PCT/KR2014/012429 filed Dec. 16, 2014, which designates the United States and was published in Korean.

TECHNICAL FIELD

The present invention relates to a recombinant microorganism having an enhanced ability to produce 1,3-propanediol and a method for producing 1,3-propanediol using the same.

BACKGROUND ART 1,3-propanediol is an alcohol (represented by $CH_2OHCH_2CH_2OH$) having three carbons and two hydroxyl (—OH) groups and can be used as a monomer for polymers such as polyesters or polyurethanes. In addition, 1,3-propanediol can be used as an additive for improving properties of cosmetics and personal care products. Particularly, polytrimethylene terephthalate (PTT) which is a linear aromatic polyester produced by polymerization of 1,3-propanediol and terephthalic acid has a unique twisted linkage called kinks created on a semi-crystal molecular structure of a polymer chain, and thus exhibits excellent elasticity and shape stability. Due to such a structural property, PPT can be used in a broad range of applications such as fibers, packages, films, non-woven fabric structures, engineering plastics, and the like.

1,3-propanediol can be synthesized by chemical synthesis and biological synthesis. As a chemical method, 1,3-propanediol can be produced by hydrogenation using ethylene oxide or acrolein as a raw material. However, this method has problems such as high cost and production of wastes containing environmental contaminants.

As a biological method, 1,3-propanediol can be produced from fermentation by recombinant *Escherichia coli* using corn derived sugars as a raw material or from fermentation by a 1,3-propanediol producing strain (1,3-propanediol natural producer) using glycerol as a raw material. A microorganism (recombinant *Escherichia coli*) which produces 1,3-propanediol using sugars derived from biomass such as corn was developed by DuPont, USA and has been used in industrialized production (WO 2001/12833). On the other hand, microorganisms capable of producing 1,3-propanediol using glycerol as a raw material has been known for over a century. Examples of such strains can include microorganisms belonging to genus *Klebsiella*, genus *Enterobacter*, genus *Clostridium*, genus *Citrobacter*, genus *Lactobacillus*, and the like. Such microorganisms produce 1,3-propanediol by a reductive metabolic pathway of glycerol and are provided with a carbon source and an energy source required for growth and a coenzyme (NAHD) required for 1,3-propanediol production by an oxidative metabolic pathway.

*Klebsiella pneumoniae* as a representative 1,3-propanediol producing microorganism is a gram negative (G(−)) bacterium, and has an excellent property of producing not only 1,3-propanediol but also 2,3-butanediol. This property can be a limitation on production of 1,3-propanediol using glycerol as a raw material since 2,3-butanediol has a boiling point similar to 1,3-propanediol, which creates problems such as making purification procedures difficult and lowering final purification yields. In order to solve these problems, research has been performed to construct variants having only a reductive metabolic pathway of producing 1,3-propanediol by employing a genetic recombination technology, i.e., by blocking an oxidative metabolic pathway of producing byproducts among glycerol metabolic pathways so as not to produce oxidative metabolic byproducts such as 2,3-butanediol. However, this method had a problem of poor 1,3-propanediol productivity, making commercial application difficult (Korean Patent Application No. 10-2008-0122166).

As a result of earnest investigation aimed at developing a recombinant microorganism capable of producing less oxidative metabolic byproducts including 2,3-butanediol upon production of 1,3-propanediol, the present inventors identified that a recombinant microorganism in which specific genes are deleted produces decreased amount of byproducts without lowering production yield and productivity of 1,3-propanediol. Based on this finding, the present invention has been completed.

DISCLOSURE

Technical Problem

It is an object of the present invention to provide a recombinant microorganism having an enhanced ability to produce 1,3-propanediol and a method for producing 1,3-propanediol using the same.

Technical Solution

In accordance with one aspect of the present invention, there is provided a recombinant microorganism for producing 1,3-propanediol, wherein a pathway for converting pyruvate into 2,3-butanediol is suppressed in a microorganism having pyruvate and acetyl-CoA biosynthetic pathways.

In accordance with another aspect of the present invention, there is provided a method for producing 1,3-propanediol, including:

culturing the recombinant microorganism according to the present invention; and harvesting 1,3-propanediol from the culture solution.

Advantageous Effects

A recombinant microorganism according to the present invention can produce 1,3-propanediol with high selectivity and yield without producing 2,3-butanediol which makes purification processes difficult by suppressing production of main byproducts including lactate, 2,3-butanediol, formic acid, and the like in a glycerol metabolic pathway.

DESCRIPTION OF DRAWINGS

FIG. 1 shows a glycerol metabolic pathway of *Klebsiella pneumoniae* which is a 1,3-propanediol producing strain.

FIG. 2 shows an operon of a 2,3-butanediol synthesis related gene in *Klebsiella pneumoniae*.

FIG. 3 shows production results of 2,3-butanediol upon batch fermentation of a recombinant strain of *Klebsiella*, Kp ΔldhA ΔpflB, wherein 2,3-BDO refers to 2,3-butanediol, and 1,3-PDO refers to 1,3-propanediol.

FIG. 4 shows production results of 2,3-butanediol upon batch fermentation of a recombinant strain of *Klebsiella*, Kp ΔldhA ΔpflB ΔbudA, wherein 2,3-BDO refers to 2,3-butanediol, and 1,3-PDO refers to 1,3-propanediol.

FIG. 5 shows production results of 2,3-butanediol upon batch fermentation of a recombinant strain of *Klebsiella*, Kp ΔldhA ΔpflB ΔbudC, wherein 2,3-BDO refers to 2,3-butanediol, and 1,3-PDO refers to 1,3-propanediol.

FIG. 6 shows production results of 2,3-butanediol upon batch fermentation of a recombinant strain of *Klebsiella*, Kp ΔldhA ΔpflB ΔbudRABC, wherein 2,3-BDO refers to 2,3-butanediol, and 1,3-PDO refers to 1,3-propanediol.

BEST MODE

The present invention relates to a recombinant microorganism for producing 1,3-propanediol, wherein a pathway for converting pyruvate into 2,3-butanediol is suppressed in a microorganism having pyruvate and acetyl-CoA biosynthetic pathways.

In addition, the present invention relates to a method for producing 1,3-propanediol, including:

culturing the recombinant microorganism according to the present invention; and harvesting 1,3-propanediol from the culture solution.

Hereinafter, the present invention will be described in detail.

Microorganism Having Pyruvate and Acetyl-CoA Biosynthetic Pathways

The microorganism according to the present invention has pyruvate and acetyl-CoA biosynthetic pathways. Herein, the acetyl-CoA biosynthetic pathway refers to a pathway for synthesizing acetyl-CoA from a specific metabolite in a microorganism. The acetyl-CoA biosynthetic pathway may also refer to a pathway for synthesizing acetyl-CoA from pyruvate. The pyruvate biosynthetic pathway refers to a pathway for synthesizing pyruvate from a specific metabolite in a microorganism. The pyruvate biosynthetic pathway may also refer to a pathway for synthesizing pyruvate from phosphoenol pyruvic acid (PEP). Preferably, the microorganism according to the present invention has pyruvate and acetyl-CoA biosynthetic pathways from a carbon source such as glycerol.

The microorganism having pyruvate and acetyl-CoA biosynthetic pathways according to the present invention is not particularly limited as long as the microorganism has the aforementioned biosynthetic pathways. In addition, the microorganism according to the present invention may be a microorganism having wild type pyruvate and acetyl-CoA biosynthetic pathways or a recombinant microorganism having pyruvate and acetyl-CoA biosynthetic pathways by genetic recombination. Preferably, the microorganism has an ability to produce 1,3-propanediol. The microorganism may be selected from the group consisting of genus *Klebsiella*, genus *Enterobacter*, and genus *Lactobacillus*. The microorganism is preferably a microorganism belonging to genus *Klebsiella*, more preferably *Klebsiella pneumoniae*.

Recombinant Microorganism for Producing 1,3-Propanediol

The recombinant microorganism for producing 1,3-propanediol according to the present invention has high 1,3-propanediol productivity and yield, and is characterized by a higher concentration of 1,3-propanediol in a fermented solution than a wild type microorganism upon fermentation. In addition, in the recombinant microorganism according to the present invention, production of oxidative byproducts such as lactate, formic acid, 2,3-butanediol and succinic acid is suppressed. Particularly, in the recombinant microorganism according to the present invention, production of 2,3-butanediol is suppressed wherein 2,3-butanediol has a boiling point similar to 1,3-propanediol as a target product, which renders purification difficult and thus lowers final purification yield. Preferably, the recombinant microorganism according to the present invention has no ability to produce formic acid, 2,3-butanediol, and succinic acid. The expression "having no ability to produce formic acid, 2,3-butanediol, and succinic acid" means that the microorganism does not produce substantial amounts of formic acid, 2,3-butanediol, and succinic acid, and means that there is no need for a separate process for removing formic acid, 2,3-butanediol, and succinic acid.

Preferably, the recombinant microorganism for producing 1,3-propanediol according to the present invention is a recombinant microorganism wherein a pathway for converting pyruvate into 2,3-butanediol is suppressed in a microorganism having pyruvate and acetyl-CoA biosynthetic pathways. More preferably, a pathway for converting pyruvate into 2,3-butanediol and a pathway for converting pyruvate into lactate are suppressed, or a pathway for converting pyruvate into 2,3-butanediol and a pathway for converting pyruvate into formic acid are suppressed. Still more preferably, a pathway for converting pyruvate into 2,3-butanediol, a pathway for converting pyruvate into lactate, and a pathway for converting pyruvate into formic acid are suppressed.

Preferably, the recombinant microorganism for producing 1,3-propanediol according to the present invention produces 1,3-propanediol with a yield of 0.40 g/g or more and a productivity of 1.5 g/L/hr or more on the basis of batch fermentation. Preferably, the recombinant microorganism has a ratio of 1,3-propanediol of 80 wt % or more in fermentation products when calculated in accordance with the following Equation 1. More preferably, the recombinant microorganism has a ratio of 1,3-propanediol of 85 wt % or more, still more preferably 88 wt % or more. Preferably, the recombinant microorganism has a ratio of lactate of less than 5 wt % in fermentation products, more preferably less than 2 wt %. Preferably, the recombinant microorganism has a ratio of formic acid of less than 1 wt % in fermentation products, more preferably less than 0.2 wt %, still more preferably less than 0.1 wt %. Preferably, the recombinant microorganism has a ratio of 2,3-butanediol of less than 1 wt % in fermentation products, more preferably less than 0.2 wt %, still more preferably less than 0.1 wt %. Preferably, the recombinant microorganism has a ratio of succinic acid of less than 1 wt % in fermentation products, more preferably less than 0.2 wt %, still more preferably less than 0.1 wt %.

Ratio of specific product in fermentation products={Concentration of specific product in fermentation products/(Total sum of concentrations of 1,3-propanediol, lactate, formic acid, 2,3-butanediol, ethanol, acetic acid, and succinic acid in fermentation products)}×100  <Equation 1>

Suppression of Pathway for Converting Pyruvate into 2,3-Butanediol

Microorganisms capable of producing 2,3-butanediol from pyruvate include a series of conversion enzymes such as α-acetolactate synthase, α-acetolactate decarboxylase, and acetoin reductase, as shown in FIG. 1. As shown in pathway 1, α-acetolactate synthase catalyzes conversion of pyruvate into α-acetolactate, α-acetolactate decarboxylase catalyzes conversion of α-acetolactate into acetoin, and acetoin reductase catalyzes conversion of acetoin into 2,3-butanediol.

<Pathway 1>

Pyruvate→α-acetolactate→acetoin→2,3-butanediol

Transcription of genes encoding enzymes involved in 2,3-butanediol synthesis is regulated by transcription activation factors, and genes encoding 2,3-butanediol synthase and transcription activation factors is present in a gene family, which is called the 2,3-butanediol operon, as shown in FIG. 2. Suppression of genes encoding enzymes on the 2,3-butanediol operon may be performed through expression suppression of each gene, suppression of enzyme activity, and the like. For example, those skilled in the art could easily suppress 2,3-butanediol synthase by selecting suitable methods, such as deleting one or more genes among budR (encodes a regulator), budA (encodes α-acetolactate decarboxylase (ALDC)), budB (encodes α-acetolactate synthetase (ALS)), and budC (encodes acetoin reductase (AR)) which are genes encoding enzymes on the 2,3-butanediol operon, causing mutations in the gene (mutations such as suppression of normal gene expression through modifying, substituting or deleting a partial nucleotide sequence or introducing a partial nucleotide sequence), regulating gene expression during transcription or translation, and the like.

Preferably, in the recombinant microorganism according to the present invention, the pathway for converting pyruvate into 2,3-butanediol is suppressed by suppressing one or more enzymes among α-acetolactate decarboxylase, α-acetolactate synthase, and acetoin reductase. More preferably, α-acetolactate decarboxylase, α-acetolactate synthase, and acetoin reductase are suppressed. Still more preferably, expression of budR, budA, budB and budC which are genes encoding the aforementioned enzymes and regulating expression thereof is suppressed.

Suppression of Pathway for Converting Pyruvate into Acetyl-CoA and Formic Acid

Pyruvate-formate lyase normally catalyzes conversion of pyruvate into acetyl-CoA and formic acid under anaerobic conditions (pathway 2).

<Pathway 2>

Pyruvate→acetyl-CoA+formic acid

A pathway for converting pyruvate into acetyl-CoA may be suppressed by suppressing pyruvate-formate lyase. Suppression of pyruvate-formate lyase may be performed by expression suppression of pyruvate-formate lyase, suppression of enzyme activity of pyruvate-formate lyase, and the like. For example, those skilled in the art could easily suppress pyruvate-formate lyase by selecting suitable methods, such as deleting pflB which is a gene encoding pyruvate-formate lyase, causing mutations in the gene (mutations such as suppression of normal gene expression through modifying, substituting or deleting a partial nucleotide sequence or introducing a partial nucleotide sequence), regulating gene expression during transcription or translation, and the like.

Suppression of Pathway for Converting Pyruvate into Lactate

Lactate dehydrogenase catalyzes conversion of pyruvate into lactate. The pathway for converting pyruvate into lactate may be suppressed by suppressing the lactate dehydrogenase. Suppression of lactate dehydrogenase may be performed by expression suppression of lactate dehydrogenase, suppression of enzyme activity of lactate dehydrogenase, and the like. For example, those skilled in the art could easily suppress lactate dehydrogenase by selecting suitable methods, such as deleting ldhA which is a gene encoding lactate dehydrogenase, causing mutations in the gene (mutations such as suppression of normal gene expression through modifying, substituting or deleting a partial nucleotide sequence or introducing a partial nucleotide sequence), regulating gene expression during transcription or translation, and the like. The recombinant microorganism in which the aforementioned pathways are suppressed exhibits lactate ratio of less than 12 wt %, more preferably less than 8 wt %, still more preferably less than 5 wt % in the fermentation products.

Method for Producing 1,3-Propanediol

The present invention relates to a method for producing 1,3-propanediol, including: culturing the recombinant microorganism according to the present invention; and harvesting 1,3-propanediol from the culture solution.

The recombinant microorganism according to the present invention may be cultured under aerobic conditions, preferably under microaerobic conditions. For example, the cultivation may be performed by supplying oxygen, namely, air, during cultivation. Specifically, the cultivation is performed by stirring, without being limited thereto.

Mode for Invention

The advantages and features of the present invention and methods for accomplishing the same will become apparent from the following examples. It should be understood that the present invention is not limited to the following examples and may be embodied in different ways, and the following examples are given to provide complete disclosure of the present invention and to provide a thorough understanding of the present invention to those skilled in the art. The present invention should be defined only by the accompanying claims and equivalents thereof.

<Materials and Methods>

Concentration of 1,3-propanediol (g/L): Amounts of 1,3-propanediol produced per unit volume Yield of 1,3-propanediol (g/g): Produced amount of 1,3-propanediol (g)/carbon source (g)

Productivity of 1,3-propanediol (g/L/h): Amounts of 1,3-propanediol produced per unit time and unit volume <Experimental Example 1> Construction of Recombinant Microorganisms Strain of *Klebsiella pneumoniae* GSC123 ΔldhA (Kp ΔldhA)

A strain of *Klebsiella pneumoniae* GSC123 ΔldhA (Kp ΔldhA) in which a lactate dehydrogenase gene (ldhA) was deleted was constructed as follows. Firstly, in order to clone a lactate dehydrogenase gene of *Klebsiella pneumoniae*, a homologous region 1 (SEQ ID NO: 2) of a target gene ldhA (SEQ ID NO: 1) was amplified using primers of SEQ ID NOs: 3 and 4 by polymerase chain reaction (PCR). Further, a homologous region 2 (SEQ ID NO: 5) was amplified using primers of SEQ ID NOs: 6 and 7 by PCR. Next, the homologous regions 1 and 2 were amplified using the same as templates for PCR, thereby obtaining a completed DNA fragment (SEQ ID NO: 8) in which the homologous regions 1 and 2 were ligated (Table 1).

The completed DNA fragment may include antibiotic resistance genes and the like in order to enhance the probability of recombination of target genes. Further, the completed DNA fragment may include a sacB gene encoding levansucrase in order to remove antibiotic resistance genes recombined in the chromosomes.

The prepared DNA fragment was transferred to wild type *Klebsiella pneumoniae* through electroporation (25 μF, 200 Ω, 18 kV/cm), in which the target gene was deleted by a homologous recombination mechanism indigenous to the microorganism.

TABLE 1

| SEQ ID NO | Sequence |
|---|---|
| 1 | ATGAAAATCGCGGTTTATAGTACGAAGCAGTACGATAAAAAGTAC<br>CTGCAGCACGTTAATGATGCATACGGCTTTGAACTGGAATTCTTC<br>GATTTCCTGCTGACAGCGAAGACTGCCAAAACCGCCAACGGTTGC<br>GAAGCGGTATGTATCTTCGTCAATGACGACGGCAGCCGCCCGGTG<br>CTGGAAGAGCTGAAGGCCCACGGGGTGAAATATATCGCCCTGCGC<br>TGCGCCGGGTTTAACAACGTCGACCTTGAGGCGGCAAAGGAGCTT<br>GGCCTGCGCGTCGTGCGCGTTCCAGCTTACTCTCCGGAAGCGGTC<br>GCTGAGCATGCGATCGGTATGATGATGTCGCTCAACCGCCGCATC<br>CACCGCGCTTACCAGCGTACCCGCGATGCCAATTTCTCCCTCGAA<br>GGCCTCACCGGCTTCACCATGTACGGCAAAACCGCCGGGGTGATC<br>GGCACCGGGAAAATTGGCGTAGCGATGTTGCGGATCCTCAAAGGC<br>TTCGGCATGCGCCTGCTGGCGTTCGACCCGTACCCAAGCGCCGCC<br>GCGCTGGAGCTGGGGGTGGAATATGTTGACCTCGCCACGCTGTAC<br>AAGGAATCGGACGTGATCTCCCTGCACTGTCCGCTGACCGACGAA<br>AACTACCACCTGCTCAATCGCGAAGCTTTCGATCAGATGAAAGAC<br>GGGGTGATGGTGATCAACACCAGCCGCGGCGCCTGATCGACTCT<br>CAGGCGGCCATCGACGCCCTGAAGCACCAGAAAATTGGCGCGCTG<br>GGGCTGGACGTTTATGAGAACGAACGCGATCGTTCTTTGAAGAC<br>AAATCCAACGACGTGATCCAGGACGATGTCTTCCGCCGCCTCTCC<br>GCCTGCCATAACGTGCTGTTTACCGGCCACCAGGCGTTCCTCACC<br>GCCGAGGCGCTGATCAGCATTTCGGAGACCACTCTGGGTAACCTG<br>CAGCAGGTCGCCAACGGCGAAACCTGTCCGAACGCCATCGTC |
| 2 | CAAGCGTGCGCGGTGAACCGGGAGAGGGATCGCTGGCCGGCAGTT<br>TGCTCAGGCAGGCGCTGTTGATCTCCAGCTGGCCAATATGCAGCC<br>GCCAGCGGCTGGGACGCGAGAGACGGGCATCGGTCACCCGGGCGA<br>TTTCACAGTCGCCCACCAGATAACGCAGATCGGGGATCAGCAGGG<br>CCGACCGCGTCAGGCGCGGGCTCTCCTGCAAAGAGATACGCGTGC<br>CCACGGGCAGCCAGATGCCCGCCAGCGTCGGCACCCAGTGGGTTA<br>GCGTCAACAGCAGGGTTAGCGGCAATAACACCAGAACTAACACCA<br>GCGCGATGGCGGCTTTATATTTACCCTTCATGGGCAGTTAATATC<br>CTGATTCAACATAAGTAAAAGCCGAAAGGCGTCCATTGTGACACG<br>TTCGACCAGTGAGTGAAAGTTTACGGCCTGTTAAAGCATAGTTGC<br>CAGCCGGACTCGCGGCGCGACGTTCGGCCATTATCATTTAACTGT<br>TGTTTAAGTCGCCCCTGCCACACTCCAGCCAGACGGGAATAGCTT<br>GCGGGAGAGGCGGTGTCGTTAATTATCTCGCTCATAGAGAGCGCA<br>CAGGACCACTATCCATGGGTATTGCTGATTGTTTTTCTGCTTACC<br>TTCACTAAATCCTGCGCATTGGTCTCGCTGGCAATCCCCGGCACC<br>TCCGGCCTGCTGCTGCTGGGGACATTCGCTTCCGCCAGCCTCGGA<br>CATTTCCTGTTAATGTGGTCCAGCGCCAGCCTCGGCGCCATCGGC<br>GGATTCTGGCTATCGTGGCGGCTGGGCATTCGCTACCGTCATCGC<br>CTCACCCATCTACGCTGGCTGACCGCCGAGCGTCTGGCCCGCAGC<br>CGCCTCTTCTTTCAGCGCTATGGCCCGTGGGCTATCTTTTTCAGC<br>CGCTTTCTCTCCCCTGAGGGCTACGCTGCCCTTCGTTAGCGGC<br>GCCAGCAGTCTGCCGCTGTGGTCGTTTCAGCTGGCTAACGTCAGC<br>TCCGGTCTGCTGTGGCCGCTTCTGCTGCTCGCCCCCGGCGCTTTC<br>AGCCTCAGTTTGTGGTGAAAAAACTTTGTCTTTCAAAGAGATTCC<br>GCAAGTCCGCGATATGCTCTAGAATTAGGATTAGCACCCTCTCAT<br>TAAACTATTTTTAATAATTGTACGATTATTTTAAATATGCTACC<br>GTGACGGTATAATCACTGGAGAAAAGTCTT |
| 3 | Kp_IdhA_FP1-TAGAGGATCCCAAGCGTGCGCGGTGAACCG |
| 4 | Kp_IdhA_RP1-GAGGAGCACAAAAGGGAAAGGCGAAGACTTTTC<br>TCCAGTGATTATAC |
| 5 | CGCCTTTCCCTTTTGTGCTCCTCTCCCGGGGGGAGCACATTCAGA<br>TAATCCCCACAGATCCCTGCTGCGATACCGTTACACTGGCTTGGT |

TABLE 1-continued

| SEQ ID NO | Sequence |
|---|---|
| | TTTATTAGTTATATGATTGTTTTGGAGTGAAAATGAACAAATTTG<br>CGGCGCTTCTGGCGGCAGGTATGCTGCTGTCCGGCTGTGTCTATA<br>ATAGTAAGGTGTCCACCGGTGCGGAACAGCTGCAGCATCATCGTT<br>TCGTGCTGACCAGCGTCAACGGCCAGGCGGTCAACGCCAGCGACC<br>GGCCGCTGGAGCTGAGCTTCGGTGAGAAGATGGCTATTACCGGCA<br>AGATGTATGTATCCGGCAATATGTGCAACGGCTTTAGCGGGGAAG<br>GTAAAGTGTCGGACGGCGAGCTGAAGGTCAAATCGCTGGCGATGA<br>CCCGGATGCTGTGCCACGACGCCCAGCTCAATACCCTGGATGCGA<br>CGATCGACAAGATGCTGCGCGAGGGTGCGCAGGTCGATCTGACGG<br>AAAACCAGTTGACGCTGGCGACCGCCGACCAGACGCTGGTCTATA<br>AGCTCGCCGACCTGATGCACTAGCCGGCGTTGAGGTGCCGCTGAC<br>GCTGCCCCGCGACGGGCCGCTGTTAGTAGCCGCAGCTGCCACCC<br>GCCAGCGCCTGCTCGCTGCAGCGTTTGCCGTTCGGCAGCGCGCAC<br>ATGCCAATCGCCGAACCATCGAGCTGACGAGCCACCGATAACGAG<br>CCGCCTATCATGGCGCAGTTGGCCTGACCGGCGTCGCTCATCGCC<br>GCCCGCATTCCCGGCGTGACGTGCGCCGCCGTGGCCTGCTGAACG<br>GGTTCACTACTGCACGCGGACAGCAACAGCGCCGCACATCCTACT<br>AACATCGCAGCTCGCATTCTCTCTCCCCTCGGAAACGTCTTAAAA<br>AAGCAAACCCCAGAATAATAGGCAGCGTGGCGGGCGGCGTCGAGA<br>GGGGAAGTACGTATTTATGCGCCTCATTAACATTTTCTAGCAAAT<br>TTTCGCCTAAAGCTTGATCTGCCTCGGCCATGTCGCCCGGCGCAG<br>GTGGTTCATCTCCCCGGCAGGCAGCCATTTTCTCCGCGAACCACGC<br>AAAATATTGATCTGGTCACGGGTACCCGGCGCATTGAGGACACAA<br>ATGCAAAAATGGCGGGTCAGCGGTTTGCTAAACTACCCCTTATA<br>TAATTACAGGGCGCGTCGCGGTTTCACGC |
| 6 | Kp_IdhA_FP2-GTATAATCACTGGAGAAAAGTCTTCGCCTTTCC<br>CTTTTGTGCTCCTC |
| 7 | Kp_IdhA_RP2-ATCGCGGCCGCGCGTGAAACCGCGACGCGCC |
| 8 | CAAGCGTGCGCGGTGAACCGGGAGAGGGATCGCTGGCCGGCAGTT<br>TGCTCAGGCAGGCGCTGTTGATCTCCAGCTGGCCAATATGCAGCC<br>GCCAGCGGCTGGGACGCGAGAGACGGGCATCGGTCACCCGGGCGA<br>TTTCACAGTCGCCCACCAGATAACGCAGATCGGGGATCAGCAGGG<br>CCGACCGCGTCAGGCGCGGGCTCTCCTGCAAAGAGATACGCGTGC<br>CCACGGGCAGCCAGATGCCCGCCAGCGTCGGCACCCAGTGGGTTA<br>GCGTCAACAGCAGGGTTAGCGGCAATAACACCAGAACTAACACCA<br>GCGCGATGGCGGCTTTATATTTACCCTTCATGGGCAGTTAATATC<br>CTGATTCAACATAAGTAAAAGCCGAAAGGCGTCCATTGTGACACG<br>TTCGACCAGTGAGTGAAAGTTTACGGCCTGTTAAAGCATAGTTGC<br>CAGCCGGACTCGCGGCGCGACGTTCGGCCATTATCATTTAACTGT<br>TGTTTAAGTCGCCCCTGCCACACTCCAGCCAGACGGGAATAGCTT<br>GCGGGAGAGGCGGTGTCGTTAATTATCTCGCTCATAGAGAGCGCA<br>CAGGACCACTATCCATGGGTATTGCTGATTGTTTTTCTGCTTACC<br>TTCACTAAATCCTGCGCATTGGTCTCGCTGGCAATCCCCGGCACC<br>TCCGGCCTGCTGCTGCTGGGGACATTCGCTTCCGCCAGCCTCGGA<br>CATTTCCTGTTAATGTGGTCCAGCGCCAGCCTCGGCGCCATCGGC<br>GGATTCTGGCTATCGTGGCGGCTGGGCATTCGCTACCGTCATCGC<br>CTCACCCATCTACGCTGGCTGACCGCCGAGCGTCTGGCCCGCAGC<br>CGCCTCTTCTTTCAGCGCTATGGCCCGTGGGCTATCTTTTTCAGC<br>CGCTTTCTCTCTCCCCTGAGGGCTACGCTGCCCTTCGTTAGCGGC<br>GCCAGCAGTCTGCCGCTGTGGTCGTTTCAGCTGGCTAACGTCAGC<br>TCCGGTCTGCTGTGGCCGCTTCTGCTGCTCGCCCCCGGCGCTTTC<br>AGCCTCAGTTTGTGGTGAAAAAACTTTGTCTTTCAAAGAGATTCC<br>GCAAGTCCGCGATATGCTCTAGAATTAGGATTAGCACCCTCTCAT<br>TAAACTATTTTTAATAATTGTACGATTATTTTAAATATGCTACC<br>GTGACGGTATAATCACTGGAGAAAAGTCTTCGCCTTTCCCTTTTG<br>TGCTCCTCTCCCGGGGGGAGCACATTCAGATAATCCCCACAGATT<br>CCTGCTGCGATACCGTTACACTGGCTTGGTTTTATTAGTTATATG<br>ATTGTTTTGGAGTGAAAATGAACAAATTTGCGGCGCTTCTGGCGG<br>CAGGTATGCTGCTGTCCGGCTGTGTCTATAATAGTAAGGTGTCCA<br>CCGGTGCGGAACAGCTGCAGCATCATCGTTTCGTGCTGACCAGCG<br>TCAACGGCCAGGCGGTCAACGCCAGCGACCGGCCGCTGGAGCTGA<br>GCTTCGGTGAGAAGATGGCTATTACCGGCAAGATGTATGTATCCG<br>GCAATATGTGCAACGGCTTTAGCGGGAAGGTAAAGTGTCGGACG<br>GCGAGCTGAAGGTCAAATCGCTGGCGATGACCCGGATGCTGTGCC<br>ACGACGCCCAGCTCAATACCCTGGATGCGACGATCGACAAGATGC<br>TGCGCGAGGGTGCGCAGGTCGATCTGACGGAAAACCAGTTGACGC<br>TGGCGACCGCCGACCAGACGCTGGTCTATAAGCTCGCCGACCTGA<br>TGCACTAGCCGGCGTTGAGGTGCCGCTGACGCTGCCCCGCGACGG<br>GCCGCTGTTAGTAGCCGCAGCTGCCACCCGCCAGCGCCTGCTCG<br>CTGCAGCGTTTGCCGTTCGGCAGCGCGCACATGCCAATCGCCGAA<br>CCATCGAGCTGACGAGCCACCGATAACGAGCCGCCTATCATGGCG<br>CAGTTGGCCTGACCGGCGTCGCTCATCGCCGCCCGCATTCCCGGC<br>GTGACGTGCGCCGCCGTGGCCTGCTGAACGGGTTCACTACTGCAC |

TABLE 1-continued

| SEQ ID NO | Sequence |
|---|---|
| | GCGGACAGCAACAGCGCCGCACATCCTACTAACATCGCAGCTCGC<br>ATTCTCTCTCCCCTCGGAAACGTCTTAAAAAAGCAAACCCCAGAA<br>TAATAGGCAGCGTGGCGGGCGGCGTCGAGAGGGGAAGTACGTATT<br>TATGCGCCTCATTAACATTTTCTAGCAAATTTTCGCCTAAAGCTT<br>GATCTGCCTCGGCCATGTCGCCCGGCGCAGGTGGTTCATCTCCCG<br>GCAGGCAGCCATTTTCTCCGCGAACCACGCAAAATATTGATCTGG<br>TCACGGGTACCCGGCGCATTGAGGACACAAATGCAAAATGGCGG<br>GGTCAGCGGTTTGCTAAACTACCCCTTATATAATTACAGGGCGCG<br>TCGCGGTTTCACGC |

Strain of *Klebsiella pneumoniae* GSC123 ΔldhA ΔpflB (Kp ΔldhA ΔpflB)

A strain of *Klebsiella pneumoniae* GSC123 ΔldhA ΔpflB (Kp ΔldhA ΔpflB) in which a pyruvate-formate lyase gene (pflB) was further deleted was constructed as follows. Firstly, in order to clone a pyruvate-formate lyase gene of *Klebsiella pneumoniae*, a homologous region 1 (SEQ ID NO: 10) of a target gene pflB (SEQ ID NO: 9) was amplified using primers of SEQ ID NOs: 11 and 12 by polymerase chain reaction (PCR). Further, a homologous region 2 (SEQ ID NO: 13) was amplified using primers of SEQ ID NOs: 14 and 15 by PCR. Next, the homologous regions 1 and 2 were amplified using the same as templates for PCR, thereby obtaining a completed DNA fragment (SEQ ID NO: 16) in which the homologous regions 1 and 2 were ligated (Table 2).

The completed DNA fragment may include antibiotic resistance genes and the like in order to enhance the probability of recombination of target genes. Further, the completed DNA fragment may include a sacB gene encoding levansucrase in order to remove antibiotic resistance genes recombined in the chromosomes.

The prepared DNA fragment was transferred to lactate dehydrogenase (ldhA) deleted *Klebsiella pneumoniae* GSC123 ΔldhA (Kp ΔldhA) through electroporation (25 μF, 200 Ω, 18 kV/cm), in which the target gene was deleted by a homologous recombination mechanism indigenous to the microorganism.

TABLE 2

| SEQ ID NO | Sequence |
|---|---|
| 9 | ATGTCCGAGCTTAATGAAAAGTTAGCCACAGCCTGGGAAGGTTTT<br>GCGAAAGGTGACTGGCAGAATGAAGTCAACGTCCGTGACTTTATT<br>CAGAAAAACTACACCCCATATGAAGGCGACGAATCCTTCCTGGCT<br>GGCGCGACTGAAGCGACCACCAAGCTGTGGGACACCGTAATGGAA<br>GGTGTAAAACAGGAAAACCGCACTCACGCGCCTGTTGATTTTGAC<br>ACTGCCCTGGCTTCCACCATCACCTCTCACGACGCGGGCTATATC<br>GAGAAAGGTCTGGAAAAAATCGTTGGTCTGCAGACCGAAGCGCCG<br>CTGAAACGTGCGATCATCCCGTTCGGTGGTATCAAATGGTTGAA<br>GGTTCCTGCAAAGCGTATAATCGCGAGCTGGACCCGATGCTGAAA<br>AAAATCTTCACAGAGTACCGTAAAACTCACAACCAGGGCGTTTTC<br>GACGTCTATACCCCGGACATTCTGCGCTGCCGTAAATCCGGCGTG<br>CTGACGGGTCTGCCGGATGCTTACGGTCGTGGTCGTATCATCGGT<br>GACTACCGTCGCGTTGCGCTGTACGGTATCGACTTCCTGATGAAA<br>GACAAATTCGCCCAGTTCAACTCTCTGCAAGCGAAACTGGAAAGC<br>GGCGAAGACCTGGAAGCGACCATCCGTCTGCGTGAAGAAATCGCT<br>GAACAACACCGCGCACTGGGCCAGATCAAAGAGATGGCCGCTAAA<br>TATGGCTATGACATCTCCGGTCCGGCGACCACCGCTCAGGAAGCG<br>ATTCAGTGGACCTACTTCGGTTACCTGGCTGCCGTGAAATCTCAG<br>AACGGCGCGGCAATGTCCTTCGGTCGTACCTCCAGCTTCCTGGAT<br>ATCTACATCGAGCGTGACCTGCAGGCGGGTAAAATCACCGAGCAA<br>GACGCGCAGGAAATGGTTGACCACCTGGTCATGAAACTGCGTATG<br>GTTCGCTTCCTGCGTACCCCGGAATATGATGAACTGTTCTCCGGC<br>GACCCGATTTGGGCAACGGAATCCATCGGCGGTATGGGCGTTGAC<br>GGCCGTACTCTGGTGACCAAAAACAGCTTCCGCTTCCTGAACACC<br>CTGTACACCATGGGGCCGTCTCCGGAGCCGAACATTACTATCCTG<br>TGGTCTGAAAAACTGCCGCTGAGCTTCAAGAAATTCGCCGCTAAA<br>GTGTCCATCGATACCTCTTCTCTGCAGTATGAGAACGATGACCTG<br>ATGCGTCCGGACTTCAACAACGACGACTACGCTATCGCATGCTGC<br>GTAAGCCCGATGGTTGTTGGTAAGCAAATGCAGTTCTTCGGCGCT<br>CGCGCTAACCTCGCGAAAACCATGCTGTACGCTATCAACGGCGGC<br>GTGGATGAAAAACTGAAAATGCAGGTTGGTCCGAAATCTGAACCG<br>ATCAAAGGCGACGTCCTGAACTTCGACGAAGTAATGGATCGCATG<br>GATCACTTCATGGACTGGCTGGCTAAACAGTACGTCACCGCGCTG<br>AACATCATCCACTACATGCACGACAAGTACAGCTACGAAGCCTCT<br>CTGATGGCGCTGCACGACCGTGACGTTATCCGCACCATGGCGTGT<br>GGTATCGCTGGTCTGTCCGTTGCTGCTGACTCCCTGTCTGCTATC<br>AAATATGCGAAAGTTAAACCGATTCGTGACGAAGACGGTCTGGCT<br>ATCGACTTCGAAATCGAAGGCGAATACCCGCAGTTTGGTAACAAC<br>GACCCTCGCGTCGATGACATGGCCGTTGACCTGGTTGAACGTTTC<br>ATGAAGAAATTCAGAAACTGCACATCACCGCAACGCTATCCCG<br>ACTCAGTCTGTTCTGACCATCACCTCTAACGTGGTGTACGGTAAG<br>CCGGTAATACCCCAGACGGTCGTCGCGCTGGCGCGCCGTTCGGTC<br>CAGGTGCTAACCCGATGCACGGCCGTGACCAGAAAGGCGCAGTAG<br>CCTCTCTGACCTCCGTCGCTAAACTGCCGTTTGCTTACGCGAAAG<br>ATGGTATCTCTTATACCTTCTCTATCGTGCCGAACGCGCTGGGTA<br>AAGACGACGAAGTTCGTAAGACCAACCTGGCGGGTCTGATGGATG<br>GTTACTTCCATCACGAAGCGTCCATCGAAGGTGGTCAGCACCTGA<br>ACGTGAACGTCATGAACCGCGAAATGCTGCTCGACGCGATGGAAA<br>ACCCGGAAAAATATCCGCAGCTGACCATCCGTGTATCTGGCTACG<br>CCGTACGTTTTAACTCCCTGACCAAAGAACAGCAGCAGGATGTTA<br>TTACCCGTACCTTCACTCAGACCATG |
| 10 | GTTTGTGCTGCTGATGTGGTTATCAGGCGAATATATGACTGCCAA<br>CGGCGGCTGGGGGCTAAACGTTCTGCAGACCGCCGACCACAAAAT<br>GCACCATACTTTTGTGGAGGCCGTGAGCCTGGGTATCCTCGCTAA<br>CCTGATGGTTTGTCTCGCCGTATGGATGAGCTATTCCGGTCGTAG<br>CCTGATGGATAAAGCGATGATCATGGTCCTGCCGGTAGCGATGTT<br>CGTTGCCAGCGGCTTTGAGCACAGCATCGCCAACATGTTTATGAT<br>CCCGATGGGTATCGTAATCCGCAACTTTGCAAGCCCGGAATTCTG<br>GACCGCCATCGGTTCGACTCCGGAAAGTTTCTCTCACTTGACCGT<br>TATGAACTTCATCACTGATAACCTGATTCCGGTAACTATCGGGAA<br>CATTATCGGCGGGGTCTGCTGGTCGGGTTGACATACTGGGTCAT<br>TTACCTGCGTGGCAACGACCATCACTAAGGGTTGTTTCAGGCAGT<br>AAATAAAAAATCCACTTAAGAAGGTAGGTGTTAC |
| 11 | Kp_pflB_FP1-GGATCCGTTTGTGCTGCTGATGTGGTTATCAG<br>GC |
| 12 | Kp_pflB_RP1-CGCCTTTTCAGTCAGACAGGGAAGTAACACCTA<br>CCTTCTTAAGTGG |
| 13 | TTCCCTGTCTGACTGAAAAGGCGTACAATAAAGGCCCCACATCAG<br>TGGGGCCTTTTTAACAAGCATTCCCCGCCCCAGCCTGCTTTGCCA<br>GTTATCTATACTTTGGGTACCTGTCAAAACAGACTCGACGCAGCC<br>GCTGAGCTGCGCACCAACACGGCCCCGGATGGGCCACATCTGGAG<br>AAAACACCGCAATGTCAGTTATTGGTCGCATTCACTCCTTTGAAT<br>CCTGTGGCACCGTTGATGGCCCAGGCATCCGCTTTATTACCTTTT<br>TCCAGGGCTGCCTGATGCGCTGCCTGTACTGCCATAACCGTGACA<br>CCTGGGATACCCACGGCGGCAAAGAAATCACCGTTGAAGAATTAA<br>TGAAAGAGGTGGTGACCTATCGTCACTTTTATGAATGCTTCCGGCG<br>GCGGCGTCACCGCCTCGGGCGGTGAGGCGATCCTGCAGGCGGAGT<br>TTGTTCGCGACTGGTTCCGCGCGTGTAAGAAGAAGGCATCCACA<br>CCTGCCTGGATACCAACGGCTTCGTACGTCGCTACGATCCGGTTA<br>TCGACGAGCTGCTGGAGGTAACAGACCTGGTGATGCTGGATCTCA<br>AGCAGATGAAC |
| 14 | Kp_pflB_FP2-CCACTTAAGAAGGTAGGTGTTACTTCCCTGTCT<br>GACTGAAAAGGCG |
| 15 | Kp_pflB_RP2-GCGGCCGCGTTCATCTGCTTGAGATCCAGCATC<br>ACC |
| 16 | GTTTGTGCTGCTGATGTGGTTATCAGGCGAATATATGACTGCCAA<br>CGGCGGCTGGGGGCTAAACGTTCTGCAGACCGCCGACCACAAAAT<br>GCACCATACTTTTGTGGAGGCCGTGAGCCTGGGTATCCTCGCTAA<br>CCTGATGGTTTGTCTCGCCGTATGGATGAGCTATTCCGGTCGTAG<br>CCTGATGGATAAAGCGATGATCATGGTCCTGCCGGTAGCGATGTT<br>CGTTGCCAGCGGCTTTGAGCACAGCATCGCCAACATGTTTATGAT |

TABLE 2-continued

| SEQ ID NO | Sequence |
|---|---|
| | CCCGATGGGTATCGTAATCCGCAACTTTGCAAGCCCGGAATTCTG
GACCGCCATCGGTTCGACTCCGGAAAGTTTCTCTCACTTGACCGT
TATGAACTTCATCACTGATAACCTGATTCCGGTAACTATCGGGAA
CATTATCGGCGGGGGTCTGCTGGTCGGGTTGACATACTGGGTCAT
TTACCTGCGTGGCAACGACCATCACTAAGGGTTGTTTCAGGCAGT
AAATAAAAAATCCACTTAAGAAGGTAGGTGTTACTTCCCTGTCTG
ACTGAAAAGGCGTACAATAAAGGCCCCACATCAGTGGGGCCTTTT
TAACAAGCATTCCCCGCCCCAGCCTGCTTTGCCAGTTATCTATAC
TTTGGGTACCTGTCAAAACAGACTCGACGCAGCCGCTGAGCTGCG
CACCAACACGGCCCCGGATGGGCCACATCTGGAGAAAACACCGCA
ATGTCAGTTATTGGTCGCATTCACTCCTTTGAATCCTGTGGCACC
GTTGATGGCCCAGGCATCCGCTTTATTACCTTTTTCCAGGGCTGC
CTGATGCGCTGCCTGTACTGCCATAACCGTGACACCTGGGATACC
CACGGCGGCAAAGAAATCACCGTTGAAGAATTAATGAAAGAGGTG
GTGACCTATCGTCACTTTATGAATGCTTCCGGCGGCGGCGTCACC
GCCTCGGGCGGTGAGGCGATCCTGCAGGCGGAGTTTGTTCGCGAC
TGGTTCCGCGCGTGTAAGAAAGAAGGCATCCACACCTGCCTGGAT
ACCAACGGCTTCGTACGTCGCTACGATCCGGTTATCGACGAGCTG
CTGGAGGTAACAGACCTGGTGATGCTGGATCTCAAGCAGATGAAC |

Strain of *Klebsiella pneumoniae* GSC123 Δ dhA ΔpflB ΔbudA (Kp ΔldhA ΔpflB ΔbudA)

A strain of *Klebsiella pneumoniae* GSC123 ΔldhA ΔpflB ΔbudA (Kp ΔldhA ΔpflB ΔbudA) in which a gene for converting α-acetolactate into acetoin (α-acetolactate decarboxylase gene, budA) on a pathway of synthesizing 2,3-butanediol was further deleted was constructed as follows. Firstly, in order to clone an α-acetolactate decarboxylase gene of *Klebsiella pneumoniae*, a homologous region 1 (SEQ ID NO: 18) of a target gene budA (SEQ ID NO: 17) was amplified using primers of SEQ ID NOs: 19 and 20 by polymerase chain reaction (PCR). Further, a homologous region 2 (SEQ ID NO: 21) was amplified using primers of SEQ ID NOs: 22 and 23 by PCR. Next, the homologous regions 1 and 2 were amplified using the same as templates for PCR, thereby obtaining a completed DNA fragment (SEQ ID NO: 24) in which the homologous regions 1 and 2 were ligated (Table 3).

The completed DNA fragment may include antibiotic resistance genes and the like in order to enhance the probability of recombination of target genes. Further, the completed DNA fragment may include a sacB gene encoding levansucrase in order to remove antibiotic resistance genes recombined in the chromosomes.

The prepared DNA fragment was transferred to lactate dehydrogenase (ldhA) and pyruvate-formate lyase (pflB) deleted *Klebsiella pneumoniae* GSC123 ΔldhA ΔpflB (Kp ΔldhA ΔpflB) through electroporation (25 μF, 200 Ω, 18 kV/cm), in which the target gene was deleted by a homologous recombination mechanism indigenous to the microorganism.

TABLE 3

| SEQ ID NO | Sequence |
|---|---|
| 17 | ATGAATCATTCTGCTGAATGCACCTGCGAAGAGAGTCTATGCGAA
ACCCTGCGGGCGTTTTCCGCGCAGCATCCCGAGAGCGTGCTCTAT
CAGACATCGCTCATGAGCGCCCTGCTGAGCGGGGTTTACGAAGGC
AGCACCACCATCGCCGACCTGCTGAAACACGGCGATTTCGGCCTC
GGCACCTTTAATGAGCTGGACGGGGAGCTGATCGCCTTCAGCAGT
CAGGTCTATCAGCTGCGCGCCGACGGCAGCGCGCGCAAAGCCCAG
CCGGAGCAGAAAACGCCGTTCGCGGTGATGACCTGGTTCCAGCCG
CAGTACCGGAAAACCTTTGACCATCCGGTGAGCCGCCAGCAGCTG
CACGAGGTGATCGACCAGCAAATCCCCTCTGACAACCTGTTCTGC
GCCCTGCGCATCGACGGCCATTTCCGCCATGCCCATACCCGCACC
GTGCCGCGCCAGACGCCGCCGTACCGGGCGATGACCGACGTACTC
GACGATCAGCCGGTGTTCCGCTTTAACCAGCGCGAAGGGGTGCTG
GTCGGCTTCCGGACCCCGCAGCATATGCAGGGGATCAACGTCGCC
GGGTATCACGAGCATTTTATTACCGATGACCGCAAAGGCGGCGGT
CACCTGCTGGATTACCAGCTCGACCACGGGGTGCTGACCTTCGGC
GAAATTCACAAGCTGATGATCGACCTGCCCGCCGACAGCGCGTTC
CTGCAGGCTAATCTGCATCCCGATAATCTCGATGCCGCCATCCGT
TCCGTAGAAAGT |
| 18 | GCAGATTAAAGGCTTTACTGCTCTCGCACGGCAGGCGGACGAAGG
CGATATCCAGCTCGGCCTCGCTCAGGGCGGTCATCAGATTGGCCA
TATTGTCTTCCATCTGGTGCAGGGTCACCCCGGGGTGGTCGAGCT
GAAAACGGTGCAGCAGCGTGAAGATTTGCGGATGGAAAGCATCAG
AACTGGTAATGCCTAGCGACAGGCTGCCGTTCATCCCGCGCGCAA
TGCCCTTGGCCTTCTCCAGCGCCGCATCGCTCATGGCGAGGATCT
GGCGGGCATCCTCATAGAAAGACTCTCCCGCTTCCGTCAGCTCCA
CCCCGCGGGTTAAACGCCGGAACAGCGGGGTCCCCACCTCGCGCT
CAAGCCGCTGAATTTGCTGACTTAACGGAGGCTGTGAAATACCCA
GCTCCTTGGCGGCCTGGGTGAAGTGCCGCGTCCTGGCGACGGCGA
CAAATAGCGAAGATAACGAAGTTCCATATCGAAAACGTCTCAAA
CCAGCATGGTTTCTATATTGGAACTGTGAGCTGAATCGGGTCAAC
ATTTATTTAACCTTTCTTATATTTGTTGAACGAGGAAGTGGTATA
TGAATCATTCTGCTGAATGCACCTGCGAACCCGATAATCTCGATG
CCGCCATCCGTTCCGTAGAAAGT |
| 19 | Kp_budA_FP1-TCTAGAGGATCCGCAGATTAAAGGCTTTACTGC
TCTC |
| 20 | Kp_budA_RP1-CGGATGGCGGCATCGAGATTATCGGGTTCGCAG
GTGCATTCAGCAGAATGATTC |
| 21 | ATGAATCATTCTGCTGAATGCACCTGCGAACCCGATAATCTCGAT
GCCGCCATCCGTTCCGTAGAAAGTTAAGGGGGTCACATGGACAAA
CAGTATCCGGTACGCCAGTGGGCGCACGGCGCCGATCTCGTCGTC
AGTCAGCTGGAAGCACAGGGGGTACGCCAGGTGTTCGGCATCCCC
GGCGCCAAAATCGACAAGGTCTTCGATTCACTGCTGGATTCCTCC
ATTCGCATTATTCCGGTACGCCACGAAGCCAACGCCGCATTTATG
GCCGCCGCCGTCGGACGTATTACCGGCAAAGCGGGCGTGGCGCTG
GTCACCTCCGGTCCGGGTTGTTCTAACCTGATCACCGGCATGGCC
ACCGCGAACAGCGAAGGCGACCCGGTGGTGGCCCTGGGCGGCGCG
GTAAAACGCGCCGATAAAGCCAAACAGGTCCACCAGAGTATGGAT
ACGGTGGCGATGTTCAGCCCGGTCACCAAATACGCCGTCGAGGTG
ACGGCGCCGGATGCGCTGGCGGAAGTGGTCTCCAACGCCTTCCGC
GCCGCCGAGCAGGGCCGGCCGGGCAGCGCGTTCGTTAGCCTGCCG
CAGGATGTGGTCGATG |
| 22 | Kp_budA_FP2-GAATCATTCTGCTGAATGCACCTGCGAACCCGA
TAATCTCGATGCCGCCATCCG |
| 23 | Kp_budA_RP2-GATCGCGGCCGCCATCGACCACATCCTGCGGCA
GG |
| 24 | GCAGATTAAAGGCTTTACTGCTCTCGCACGGCAGGCGGACGAAGG
CGATATCCAGCTCGGCCTCGCTCAGGGCGGTCATCAGATTGGCCA
TATTGTCTTCCATCTGGTGCAGGGTCACCCCGGGGTGGTCGAGCT
GAAAACGGTGCAGCAGCGTGAAGATTTGCGGATGGAAAGCATCAG
AACTGGTAATGCCTAGCGACAGGCTGCCGTTCATCCCGCGCGCAA
TGCCCTTGGCCTTCTCCAGCGCCGCATCGCTCATGGCGAGGATCT
GGCGGGCATCCTCATAGAAAGACTCTCCCGCTTCCGTCAGCTCCA
CCCCGCGGGTTAAACGCCGGAACAGCGGGGTCCCCACCTCGCGCT
CAAGCCGCTGAATTTGCTGACTTAACGGAGGCTGTGAAATACCCA
GCTCCTTGGCGGCCTGGGTGAAGTGCCGCGTCCTGGCGACGGCGA
CAAATAGCGAAGATAACGAAGTTCCATATCGAAAACGTCTCAAA
CCAGCATGGTTTCTATATTGGAACTGTGAGCTGAATCGGGTCAAC
ATTTATTTAACCTTTCTTATATTTGTTGAACGAGGAAGTGGTATA
TGAATCATTCTGCTGAATGCACCTGCGAACCCGATAATCTCGATG
CCGCCATCCGTTCCGTAGAAAGTTAAGGGGGTCACATGGACAAAC
AGTATCCGGTACGCCAGTGGGCGCACGGCGCCGATCTCGTCGTCA
GTCAGCTGGAAGCACAGGGGGTACGCCAGGTGTTCGGCATCCCCG
GCGCCAAAATCGACAAGGTCTTCGATTCACTGCTGGATTCCTCCA
TTCGCATTATTCCGGTACGCCACGAAGCCAACGCCGCATTTATGG
CCGCCGCCGTCGGACGTATTACCGGCAAAGCGGGCGTGGCGCTGG
TCACCTCCGGTCCGGGTTGTTCTAACCTGATCACCGGCATGGCCA
CCGCGAACAGCGAAGGCGACCGGTGGTGGCCCTGGGCGGCGCGG
TAAAACGCGCCGATAAAGCCAAACAGGTCCACCAGAGTATGGATA |

TABLE 3-continued

| SEQ ID NO | Sequence |
|---|---|
| | CGGTGGCGATGTTCAGCCCGGTCACCAAATACGCCGTCGAGGTGA<br>CGGCGCCGGATGCGCTGGCGGAAGTGGTCTCCAACGCCTTCCGCG<br>CCGCCGAGCAGGGCCGGCCGGGCAGCGCGTTCGTTAGCCTGCCGC<br>AGGATGTGGTCGATG |

Strain of *Klebsiella pneumoniae* GSC123 ΔldhA ΔpflB ΔbudC (Kp ΔldhA ΔpflB ΔbudC)

A strain of *Klebsiella pneumoniae* GSC123 ΔldhA ΔpflB ΔbudC (Kp ΔldhA ΔpflB ΔbudC) in which acetoin reductase gene, budC for converting acetoin into 2,3-butanediol on a pathway of synthesizing 2,3-butanediol, was further deleted was constructed as follows. Firstly, in order to clone an acetoin reductase gene of *Klebsiella pneumoniae*, a homologous region 1 (SEQ ID NO: 26) of a target gene budC (SEQ ID NO: 25) was amplified using primers of SEQ ID NOs: 27 and 28 by polymerase chain reaction (PCR). Further, a homologous region 2 (SEQ ID NO: 29) was amplified using primers of SEQ ID NOs: 30 and 31 by PCR. Next, the homologous regions 1 and 2 were amplified using the same as templates for PCR, thereby obtaining a completed DNA fragment (SEQ ID NO: 32) in which the homologous regions 1 and 2 were ligated (Table 4).

The completed DNA fragment may include antibiotic resistance genes and the like in order to enhance the probability of recombination of target genes. Further, the completed DNA fragment may include a sacB gene encoding levansucrase in order to remove antibiotic resistance genes recombined in the chromosomes.

The prepared DNA fragment was transferred to lactate dehydrogenase (ldhA) and pyruvate-formate lyase (pflB) deleted *Klebsiella pneumoniae* GSC123 ΔldhA ΔpflB (Kp ΔldhA ΔpflB) through electroporation (25 μF, 200 Ω, 18 kV/cm), in which the target gene was deleted by a homologous recombination mechanism indigenous to the microorganism.

TABLE 4

| SEQ ID NO | Sequence |
|---|---|
| 25 | ATGAAAAAAGTCGCACTTGTTACCGGCGCCGGCCAGGGGATTGGT<br>AAAGCTATCGCCCTTCGTCTGGTGAAGGATGGATTTGCCGTGGCC<br>ATTGCCGATTATAACGACGCCACCGCCAAAGCGGTCGCCTCCGAA<br>ATCAACCAGGCCGGCGGCCGCGCGCCATGGCGGTGAAAGTGGATGTT<br>TCTGACCGCGACCAGGTATTTGCCGCCGTCGAACAGGCGCGCAAA<br>ACGCTGGGCGGCTTCGACGTCATCGTCAACAACGCCGGCGTGGCG<br>CCATCCACGCCGATCGAGTCCATTACCCCGGAGATTGTCGACAAA<br>GTCTACAACATCAACGTCAAAGGGGTGATCTGGGGCATCCAGGCA<br>GCGGTCGAGGCCTTTAAGAAAGAGGGTCACGGCGGGAAAATCATC<br>AACGCCTGTTCCCAGGCCGGCCACGTCGGCAACCCGGAGCTGGCG<br>GTATATAGCTCGAGTAAATTCGCGGTACGCGGCTTAACCCAGACC<br>GCCGCTCGCGACCTCGCGCCGCTGGGCATCACGGTCAACGGCTAC<br>TGCCCGGGGATTGTCAAAACGCCGATGTGGGCCGAAATTGACCGC<br>CAGGTGTCCGAAGCCGCCGGTAAACCGCTGGGCTACGGTACCGCC<br>GAGTTCGCCAAACGCATCACCCTCGGCCGCCTGTCCGAGCCGGAA<br>GATGTCGCCGCCTGCGTCTCCTATCTTGCCAGCCCGGATTCTGAT<br>TATATGACCGGTCAGTCATTGCTGATCGACGGCGGCATGGTGTTT<br>AAC |
| 26 | GCTGCGTATCGTTCGCGCCATGCAGGACATCGTCAACAGCGACGT<br>CACGTTGACCGTGGACATGGGCAGCTTCCATATCTGGATTGCCCG<br>CTACCTGTACAGCTTCCGCGCCCGCCAGGTGATGATCTCCAACGG<br>CCAGCAGACCATGGGCGTCGCCCTGCCCTGGGCCATCGGCGCCTG<br>GCTGGTCAATCCTGAGCGCAAAGTGGTCTCCGTCTCCGGCGACGG<br>CGGCTTCCTGCAGTCGAGCATGGAGCTGGAGACCGCCGTCCGCCT |
|  | GAAAGCCAACGTGCTGCACCTGATCTGGGTCGATAACGGCTACAA<br>CATGGTGGCCATTCAGGAAGAGAAAAAATACCAGCGCCTGTCCGG<br>CGTCGAGTTTGGGCCGATGGATTTTAAAGCCTATGCCGAATCCTT<br>CGGCGCGAAAGGGTTTGCCGTGGAAAGCGCCGAGGCGCTGGAGCC<br>GACCCTGCGCGCGGCGATGGACGTCGACGGCCCGGCGGTAGTGGC<br>CATCCCGGTGGATTATCGCGATAACCCGCTGCTGATGGGCCAGCT<br>GCATCTGAGTCAGATTCTGTAAGTCATCACAATAAGGAAAGAAAA<br>ATGAAAAAAGTCGCACTTGTTACCGGCGCCATGACCGGTCAGTCA<br>TTGCTGATCG |
| 27 | Kp_budC_FP1-TCTAGAGGATCCGCTGCGTATCGTTCGCGC<br>CATGC |
| 28 | Kp_budC_RP1-CGATCAGCAATGACTGACCGGTCATGGCGCCGG<br>TAACAAGTGCGACTT |
| 29 | AAGTCGCACTTGTTACCGGCGCCATGACCGGTCAGTCATTGCTGA<br>TCGACGGCGGCATGGTGTTTAACTAATAAAAAAAAGCTCTGACAT<br>GGCTTGCCCCTGCTTTCGCGCAGGGGCTTTTTTTGGTTTGGGTGT<br>AAGTGTAAGCATCCCGGAGAAACGAAGCATCGATATTTGAGGGCT<br>TCTGGCGTTCTCACTTACGCTTCGACACGACGTGGGCAATCTGAC<br>TGGGATGAAGGTCTGATTTGAGCGAGGAGCGGAAGTTCGGGAACG<br>GGATAGCTCTGACCTGCCACCAGGATTAGATACAACCGTCAGTTA<br>GTAAGGTCGGTTTGTTTACCTTCACATTTTCCATTTCGCCACCGT<br>GCTGCAAACTCTGATGGCGTCTGATAATTCAGTGCTGAATGTGGA<br>CGACACTCGTTATAATCCTGCCGCCAGTCATTAATGATTTTCCTT<br>GCGTGAACGATATCGCTGAACCAGTGCTCATTCAGGCATTCATCG<br>CGAAATCGTCCGTTAAAGCTCTCAATAAATCCGTTCTGCGTTGGC<br>TTGCCCGGCTGGATTAAGCGCAACTCAACACCATGCTCAAAGGCC<br>CATTGATCCAGTGCACGGCAAGTGAACTCCGGCCCCTGG |
| 30 | Kp_budC_FP2-AAGTCGCACTTGTTACCGGCGCCATGACCGGTC<br>AGTCATTGCTGATCG |
| 31 | Kp_budC_RP2-GCGGCCGCCCAGGGGCCGGAGTTCACTTGCC |
| 32 | GCTGCGTATCGTTCGCGCCATGCAGGACATCGTCAACAGCGACGT<br>CACGTTGACCGTGGACATGGGCAGCTTCCATATCTGGATTGCCCG<br>CTACCTGTACAGCTTCCGCGCCCGCCAGGTGATGATCTCCAACGG<br>CCAGCAGACCATGGGCGTCGCCCTGCCCTGGGCCATCGGCGCCTG<br>GCTGGTCAATCCTGAGCGCAAAGTGGTCTCCGTCTCCGGCGACGG<br>CGGCTTCCTGCAGTCGAGCATGGAGCTGGAGACCGCCGTCCGCCT<br>GAAAGCCAACGTGCTGCACCTGATCTGGGTCGATAACGGCTACAA<br>CATGGTGGCCATTCAGGAAGAGAAAAAATACCAGCGCCTGTCCGG<br>CGTCGAGTTTGGGCCGATGGATTTTAAAGCCTATGCCGAATCCTT<br>CGGCGCGAAAGGGTTTGCCGTGGAAAGCGCCGAGGCGCTGGAGCC<br>GACCCTGCGCGCGGCGATGGACGTCGACGGCCCGGCGGTAGTGGC<br>CATCCCGGTGGATTATCGCGATAACCCGCTGCTGATGGGCCAGCT<br>GCATCTGAGTCAGATTCTGTAAGTCATCACAATAAGGAAAGAAAA<br>ATGAAAAAAGTCGCACTTGTTACCGGCGCCATGACCGGTCAGTCA<br>TTGCTGATCGACGGCGGCATGGTGTTTAACTAATAAAAAAAAGCT<br>CTGACATGGCTTGCCCCTGCTTTCGCGCAGGGGCTTTTTTTGGTT<br>TGGGTGTAAGTGTAAGCATCCCGGAGAAACGAAGCATCGATATTT<br>GAGGGCTTCTGGCGTTCTCACTTACGCTTCGACACGACGTGGGCA<br>ATCTGACTGGGATGAAGGTCTGATTTGAGCGAGGAGCGGAAGTTC<br>GGGAACGGGATAGCTCTGACCTGCCACCAGGATTAGATACAACCG<br>TCAGTTAGTAAGGTCGGTTTGTTTACCTTCACATTTTCCATTTCG<br>CCACCGTGCTGCAAACTCTGATGGCGTCTGATAATTCAGTGCTGA<br>ATGTGGACGACACTCGTTATAATCCTGCCGCCAGTCATTAATGAT<br>TTTCCTTGCGTGAACGATATCGCTGAACCAGTGCTCATTCAGGCA<br>TTCATCGCGAAATCGTCCGTTAAAGCTCTCAATAAATCCGTTCTG<br>CGTTGGCTTGCCCGGCTGGATTAAGCGCAACTCAACACCATGCTC<br>AAAGGCCCATTGATCCAGTGCACGGCAAGTGAACTCCGGCCCCTG<br>G |

Strain of *Klebsiella pneumoniae* GSC123 ΔldhA ΔpflB ΔbudRABC (Kp ΔldhA ΔpflB ΔbudRABC)

A strain of *Klebsiella pneumoniae* GSC123 ΔldhA ΔpflB ΔbudRABC (Kp ΔldhA ΔpflB ΔbudRABC) in which genes (budRABC) constituting a 2,3-butanediol operon, namely, a gene for transcription activation factors (budR), a gene for α-acetolactate decarboxylase (budA), a gene for α-acetolactate synthase (budB), and a gene for acetoin reductase (budC) were further deleted was constructed as follows.

Firstly, in order to clone a gene for a 2,3-butanediol operon of *Klebsiella pneumoniae*, a homologous region 1 (SEQ ID NO: 34) of a target gene budRABC (SEQ ID NO: 33) was amplified using primers of SEQ ID NOs: 35 and 36 by polymerase chain reaction (PCR). Further, a homologous region 2 (SEQ ID NO: 37) was amplified using primers of SEQ ID NOs: 38 and 39 by PCR. Next, the homologous regions 1 and 2 were amplified using the same as templates for PCR, thereby obtaining a completed DNA fragment (SEQ ID NO: 40) in which the homologous regions 1 and 2 were ligated (Table 5).

The completed DNA fragment may include antibiotic resistance genes and the like in order to enhance the probability of recombination of target genes. Further, the completed DNA fragment may include a sacB gene encoding levansucrase in order to remove antibiotic resistance genes recombined in the chromosomes.

The prepared DNA fragment was transferred to lactate dehydrogenase (ldhA) and pyruvate-formate lyase (pflB) deleted *Klebsiella pneumoniae* GSC123 ΔldhA ΔpflB (Kp ΔldhA ΔpflB) through electroporation (25 μF, 200 Ω, 18 kV/cm) in which the target gene was deleted by a homologous recombination mechanism indigenous to the microorganism.

TABLE 5

| SEQ ID NO | Sequence |
|---|---|
| 33 | GAACATCGCCAGAAAGCGTTTCACCGTACGCGAGCGCTCGAAGCG<br>CCGCCAGGCGATGGCGATATCGGTCTTCAGCGGCGCCCCGCTAAG<br>CGGGTGATAGCTGACGTTCGGCTGCTGGATGCAGGTCATCGACTG<br>CGGAACCAGCGCGAAGCCGAAGCCAGCATTGACCATGCTCAGCGA<br>CGACGAAATTTGCGACGACTGCCAGGCGCGCTCCATATCGATCCC<br>GGCGCGCAGACAGCTGTTGTACACCAGCTCATACAGCCCGGGGGC<br>CACCTCCCGCGGGAAGAGGATCGGCGCCACGTCGCGCAGCTGCTC<br>CAGGGCCAGGGTCGGCTGCGTCGCCAGCGGGTTATCGCGCGGCAG<br>CGCGATAACCATCGGCTCCTCATCGATAATCCGCAGATTAAAGGC<br>TTTACTGCTCTCGCACGGCAGGCGGACGAAGGCGATATCCAGCTC<br>GGCCTCGCTCAGGGCGGTCATCAGATTGGCCATATTGTCTTCCAT<br>CTGGTGCAGGGTCACCCCGGGGTGGTCGAGCTGAAAACGGTGCAG<br>CAGCGTGAAGATTTGCGGATGGAAAGCATCAGAACTGGTAATGCC<br>TAGCGACAGGCTGCCGTTCATCCCGCGCGCAATGCCCTTGGCCTT<br>CTCCAGCGCCGCATCGCTCATGGCGAGGATCTGGCGGGCATCCTC<br>ATAGAAAGACTCTCCCGCTTCCGTCAGCTCCACCCCGCGGGTTAA<br>ACGCCGGAACAGCGGGGTCCCCACCTCGCGCTCAAGCCGCTGAAT<br>TTGCTGACTTAACGGAGGCTGTGAAATACCCAGCTCCTTGGCGGC<br>CTGGGTGAAGTGCCGCGTCCTGGCGACGGCGACAAAATAGCGAAG<br>ATAACGAAGTTCCATATCGAAAACGTCTCAAACCAGCATGGTTTC<br>TATATTGGAACTGTGAGCTGAATCGGGTCAACATTTATTTAACCT<br>TTCTTATATTTGTTGAACGAGGAAGTGGTATATGAATCATTCTGC<br>TGAATGCACCTGCGAAGAGAGTCTATGCGAAACCCTGCGGGCGTT<br>TTCCGCGCAGCATCCCGAGAGCGTGCTCTATCAGACATCGCTCAT<br>GAGCGCCCTGCTGAGCGGGGTTTACGAAGGCAGCACCACCATCGC<br>CGACCTGCTGAAACACGGCGATTTCGGCCTCGGCACCTTTAATGA<br>GCTGGACGGGGAGCTGATCGCCTTCAGCAGTCAGGTCTATCAGCT<br>GCGCGCCGACGGCAGCGCCGCACAAAGCCCAGCCGGAGCAGAAAC<br>GCCGTTCGCGGTGATGACCTGGTTCCAGCCGCAGTACCGGAAAAC<br>CTTTGACCATCCGGTGAGCCGCCAGCAGCTGCACGAGGTGATCGA<br>CCAGCAAATCCCCTCTGACAACCTGTTCTGCGCCCTGCGCATCGA<br>CGGCCATTTCCGCCATGCCCATACCCGCACCGTGCCGCGCCAGAC<br>GCCGCCGTACCGGGCGATGACCGACGTACTCGACGATCAGCCGGT<br>GTTCCGCTTTAACCAGCGCGAAGGGGTGCTGGTCGGCTTCCGGAC<br>CCCGCAGCATATGCAGGGGATCAACGTCGCCGGGTATCACGAGCA<br>TTTTATTACCGATGACCGCAAAGGCGGCGGTCACCTGCTGGATTA<br>CCAGCTCGACCACGGGGTGCTGACCTTCGGCGAAATTCACAAGCT<br>GATGATCGACCTGCCCGCCGACAGCGCGTTCCTGCAGGCTAATCT<br>GCATCCCGATAATCTCGATGCCGCCATCCGTTCCGTAGAAAGTTA<br>AGGGGGTCACATGGACAAACAGTATCCGGTACGCCAGTGGCCACA<br>CGGCGCCGATCTCGTCGTCAGTCAGCTGGAAGCACAGGGGGTACG<br>CCAGGTGTTCGGCATCCCCGGCGCCAAAATCGACAAGGTCTTCGA<br>TTCACTGCTGGATTCCTCCATTCGCATTATTCCGGTACGCCACGA<br>AGCCAACGCCGCATTTATGGCCGCCGCCGTCGGACGTATTACCGG<br>CAAAGCGGGCGTGGCGCTGGTCACCTCCGGTCCGGGTTGTTCTAA<br>CCTGATCACCGGCATGGCCACCGCGAACAGCGAAGGCGACCCGGT<br>GGTGGCCCTGGGCGGCGCGGTAAAACGCGCCGATAAAGCCAAACA<br>GGTCCACCAGAGTATGGATACGGTGGCGATGTTCAGCCCGGTCAC<br>CAAATACGCCGTCGAGGTGACGGCGCCGGATGCGCTGGCGGAAGT<br>GGTCTCCAACGCCTTCCGCGCCGCCGAGCAGGGCCGGCCGGGCAG<br>CGCGTTCGTTAGCCTGCCGCAGGATGTGGTCGATGGCCCGGTCAG<br>CGGCAAAGTACTGCCGGCCAGCGGGGCCCCGCAGATGGGCGCCGC<br>GCCGGATGATGCCATCGACCAGGTGCGAAGCTTATCGCCCAGGC<br>GAAGAACCCGATCTTCCTGCTCGGCCTGATGGCCAGCCAGCCGGA<br>AAACAGCAAGGCGCTGCGCCGTTTGCTGGAGACCAGCCATATTCC<br>AGTCACCAGCACCTATCAGGCCGCCGGAGCGGTGAATCAGGATAA<br>CTTCTCTCGCTTCGCCGGCCGGGTTGGGCTGTGTTTAACAACCAGGC<br>CGGGGACCGTCTGCTGCAGCTTGCCGACCTGGTGATCTGCATCGG<br>CTACAGCCCGGTGGAATACGAACCGGCGATGTGGAACAGCGGCAA<br>CGCGACGCTGGTGCACATCGACGTGCTGCCCGCCTATGAAGAGCG<br>CAACTACACCCCGGATGTCGAGCTGGTAGGCGATATCGCCGGCAC<br>TCTCAACAAGCTGGCGCAAAATATCGATCATCGGCTGGTGCTCTC<br>CCCGCAGGCAGCGGAGATCCTCCGCGACCGCCAGCACCAGCGCGA<br>GCTGCTGGACCGCCGCGGCGCGCAGCTCAACCAGTTTGCCCTGCA<br>TCCGCTGCGTATCGTTCGCGCCATGCAGGACATCGTCAACAGCGA<br>CGTCACGTTGACCGTGGACATGGGCAGCTTCCATATCTGGATTGC<br>CCGCTACCTGTACAGCTTCCGCGCCCGCCAGGTGATGATCTCCAA<br>CGGCCAGCAGACCATGGGCGTCGCCCTGCCCTGGGCCATCGGCGC<br>CTGGCTGGTCAATCCTGAGCGCAAAGTGGTCTCCGTCTCCGGCGA<br>CGGCGGCTTCCTGCAGTCGAGCATGGAGCTGGAGACCGCCGTCCG<br>CCTGAAAGCCAACGTGCTGCACCTGATCTGGGTCGATAACGGCTA<br>CAACATGGTGGCCATTCAGGAAGAGAAAAAATACCAGCGCCTGTC<br>CGGCGTCGAGTTTGGGCCGATGGATTTTAAAGCCTATGCCGAATC<br>CTTCGGCGCGAAAGGGTTTGCCGTGGAAAGCGCCGAGGCGCTGGA<br>GCCGACCCTGCGCGCGGCGATGGACGTCGACGGCCCGGCGGTAGT<br>GGCCATCCCGGTGGATTATCGCGATAACCCGCTGCTGATGGGCCA<br>GCTGCATCTGAGTCAGATTCTGTAAGTCATCACAATAAGGAAAGA<br>AAAATGAAAAAAGTCGCACTTGTTACCGGCGCCGGCCAGGGGATT<br>GGTAAAGCTATCGCCCTTCGTCTGGTGAAGGATGGATTTGCCGTG<br>GCCATTGCCGATTATAACGACGCCACCGCCAAAGCGGTCGCCTCC<br>GAAATCAACCAGGCCGGCGGCCGCGCCATGGCGGTGAAAGTGGAT<br>GTTTCTGACCGCGACCAGGTATTTGCCGCCGTCGAACAGGCGCGC<br>AAAACGCTGGGCGGCTTCGACGTCATCGTCAACAACGCCGGCGTG<br>GCGCCATCCACGCCGATCGAGTCCATTACCCCGGAGATTGTCGAC<br>AAAGTCTACAACATCAACGTCAAAGGGGTGATCTGGGGCATCCAG<br>GCAGCGGTCGAGGCCTTTAAGAAAGAGGGTCACGGCGGGAAAATC<br>ATCAACGCCTGTTCCCAGGCCGGCCACGTCGGCAACCCGGAGCTG<br>GCGGTATATAGCTCGAGTAAATTCGCGGTACGCGGCTTAACCCAG<br>ACCGCCGCTCGCGACCTCGCGCCGCTGGGCATCACGGTCAACGGC<br>TACTGCCCGGGGATTGTCAAAACGCCGATGTGGGCCGAAATTGAC<br>CGCCAGGTGTCCGAAGCCGCCGGTAAACCGCTGGGCTACGGTACC<br>GCCGAGTTCGCCAAACGCATCACCCTCGGCCGCCTGTCCGAGCCG<br>GAAGATGTCGCCGCCTGCGTCTCCTATCTTGCCAGCCCGGATTCT<br>GATTATATGACCGGTCAGTCATTGCTGATCGACGGCGGCATGGTG<br>TTTAAC |
| 34 | CCAGCTGGTGCTCAATGGCTTCGGCGACAGCAGCCACGCCCGGGC<br>TGAAGTCGCCGCGCTGGGCAAGATCCCCGGCTATCACGACGCCGA<br>CCTGCGCGACGTCGGGCAGATCGAGGCGATGATGCGCTATGCCGA<br>AAGCACCTTCGGCGGCGTCGATATCGTGATCAATAACGCCGGCAT<br>CCAGCACGTGGCCCCGGTGGAGCAGTTCCCGGTGGACAAATGGAA<br>CGATATTCTCGCCATCAATCTCTCCAGCGTCTTCCACACCACCCG<br>CCTGGCGCTGCCGGGTATGCGCCAGCGCAACTGGGGCGCATCAT<br>CAACATTGCCTCAGTGCATGGCCTGGTGGCGTCGAAAGAGAAATC<br>GGCCTACGTCGCCGCCAAGCACGCGGTGGTCGGGCTGACCAAAAC<br>CGTGGCCCTGGAAACCGCGCGCAGCGGTATCACCTGCAACGCCAT<br>CTGCCCTGGCTGGGTGCTAACCCCGCTGGTGCAGCAGCAGATCGA<br>CAAACGCATCGCCGAGGGGGTCGACCCGGAGCAGGCCAGCGCCCA<br>GCTGCTGGCGGAAAAACAGCCCTCCGGGGAGTTTGTCACCCCGCA<br>GCAGCTGGGCGAAATGGCGCTGTTTCTGTGCAGCGATGCCGCCGC<br>CCAGGTGCGCGGCGCCGCATGGAACATGGATGGCGGCTGGGTGGC<br>GCAGTAAGCCGCTGGCGCCGCGAAGA |

TABLE 5-continued

| SEQ ID NO | Sequence |
|---|---|
| 35 | Kp_budRABC_FP1-TAGAGGATCCCCAGCTGGTGCTCAATGGCTTCG |
| 36 | Kp_budRABC_RP1-CAAGCCATGTCAGAGCTTTTTTTATCTTCGCGGCGCCAGCGGC |
| 37 | TAAAAAAAAGCTCTGACATGGCTTGCCCCTGCTTTCGCGCAGGGGCTTTTTTTGGTTTGGGTGTAAGTGTAAGCATCCCGGAGAAACGAAGCATCGATATTTGAGGGCTTCTGGCGTTCTCACTTACGCTTCGACACGACGTGGGCAATCTGACTGGGATGAAGGTCTGATTTGAGCGAGGAGCGGAAGTTCGGGAACGGGATAGCTCTGACCTGCCACCAGGATTAGATACAACCGTCAGTTAGTAAGGTCGGTTTGTTTACCTTCACATTTTCCATTTCGCCACCGTGCTGCAAACTCTGATGGCGTCTGATAATTCAGTGCTGAATGTGGACGACACTCGTTATAATCCTGCCGCCAGTCATTAATGATTTTCCTTGCGTGAACGATATCGCTGAACCAGTGCTCATTCAGGCATTCATCGCGAAATCGTCCGTTAAAGCTCTCAATAAATCCGTTCTGCGTTGGCTTGCCCGGCTGGATTAAGCGCAACTCAACACCATGCTCAAAGGCCCATTGATCCAGTGCACGGCAAGTGAACTCCGGCCCCTGGTCAGTTCTTATCGTCGCCGGATAGCCTCGAAACAGTGCAATGCTGTCCAGAATACGCGAGACCTGAACGCCTGAAATCCCAAAGGCAACAGTGACCGTCAGGCATTCCTTTGTGAAATCATCGACGCAGGTAAGACACTTGATCCTGC |
| 38 | Kp_budRABC_FP2-GCCGCTGGCGCCGCGAAGATAAAAAAAGCTCTGACATGGCTTG |
| 39 | Kp_budRABC_RP2-GATCGCGGCCGCGCAGGATCAAGTGTCTTACCTGCG |
| 40 | CCAGCTGGTGCTCAATGGCTTCGGCGACAGCAGCCACGCCCGGCTGAAGTCGCCGCGCTGGGCAAGATCCCCGGCTATCACGACGCCGACCTGCGCGACGTCGGGCAGATCGAGGCGATGATGCGCTATGCCGAAAGCACCTTCGGCGGCGTCGATATCGTGATCAATAACGCCGGCATCCAGCACGTGGCCCCGGTGGAGCAGTTCCCGGTGGACAAATGGAACGATATTCTCGCCATCAATCTCTCCAGCGTCTTCCACACCACCCGCCTGGCGCTGCCGGGTATGCGCCAGCGCAACTGGGGCGCATCATCAACATTGCCTCAGTGCATGGCCTGGTGGCGTCGAAAGAGAAATCGGCCTACGTCGCCGCCAAGCACGCGGTGGTCGGGCTGACCAAAACCGTGGCCCTGGAAACCGCGCGCAGCGGTATCACCTGCAACGCCATCTGCCCTGGCTGGGTGCTAACCCCGCTGGTGCAGCAGCAGATCGACAAACGCATCGCCGAGGGGGTCGACCCGGAGCAGGCCAGCGCCCAGCTGCTGGCGGAAAAACAGCCCTCCGGGGAGTTTGTCACCCCGCAGCAGCTGGGCGAAATGGCGCTGTTTCTGTGCAGCGATGCCGCCGCCCAGGTGCGCGGCGCCGCATGGAACATGGATGGCGGCTGGGTGGCGCAGTAAGCCGCTGGCGCCGCGAAGATAAAAAAAGCTCTGACATGGCTTGCCCCTGCTTTCGCGCAGGGGCTTTTTTTGGTTTGGGTGTAAGTGTAAGCATCCCGGAGAAACGAAGCATCGATATTTGAGGGCTTCTGGCGTTCTCACTTACGCTTCGACACGACGTGGGCAATCTGACTGGGATGAAGGTCTGATTTGAGCGAGGAGCGGAAGTTCGGGAACGGGATAGCTCTGACCTGCCACCAGGATTAGATACAACCGTCAGTTAGTAAGGTCGGTTTGTTTACCTTCACATTTTCCATTTCGCCACCGTGCTGCAAACTCTGATGGCGTCTGATAATTCAGTGCTGAATGTGGACGACACTCGTTATAATCCTGCCGCCAGTCATTAATGATTTTCCTTGCGTGAACGATATCGCTGAACCAGTGCTCATTCAGGCATTCATCGCGAAATCGTCCGTTAAAGCTCTCAATAAATCCGTTCTGCGTTGGCTTGCCCGGCTGGATTAAGCGCAACTCAACACCATGCTCAAAGGCCCATTGATCCAGTGCACGGCAAGTGAACTCCGGCCCCTGGTCAGTTCTTATCGTCGCCGGATAGCCTCGAAACAGTGCAATGCTGTCCAGAATACGCGAGACCTGAACGCCTGAAATCCCAAAGGCAACAGTGACCGTCAGGCATTCCTTTGTGAAATCATCGACGCAGGTAAGACACTTGATCCTGC |

The genotypes of recombinant strains of *Klebsiella pneumoniae* constructed for the present invention are as summarized in Table 6.

TABLE 6

| Recombinant strains | Description |
|---|---|
| KpΔldhA | *Klebsiella pneumoniae* GSC123 in which a gene for lactate dehydrogenase (ldhA) is deleted |
| KpΔldhA ΔpflB | *Klebsiella pneumoniae* GSC123 in which a gene for lactate dehydrogenase (ldhA) and a gene for pyruvate-formate lyase (pflB) are deleted |
| KpΔldhA ΔpflBΔbudA | *Klebsiella pneumoniae* GSC123 in which a gene for lactate dehydrogenase (ldhA), a gene for pyruvate-formate lyase (pflB) and a gene for α-acetolactate decarboxylase (budA) are deleted |
| KpΔldhA ΔpflB ΔbudC | *Klebsiella pneumoniae* GSC123 in which a gene for lactate dehydrogenase (ldhA), a gene for pyruvate-formate lyase (pflB) and a gene for acetoin reductase (budC) are deleted |
| KpΔldhA ΔpflB ΔbudRABC | *Klebsiella pneumoniae* GSC123 in which a gene for lactate dehydrogenase (ldhA), a gene for pyruvate-formate lyase (pflB) and a gene for 2,3-butanediol operon (budRABC) are deleted |

<Experimental Example 2> Production of 1,3-Propanediol

The recombinant strains constructed in Experimental Example 1 were cultured, thereby producing 1,3-propanediol. As a control for comparison, a wild type *Klebsiella pneumoniae* GSC123 (Kp wt) was used.

250 ml of a complex medium was inoculated with each recombinant strain, followed by culturing at 37° C. for 16 hours. 3 L of complex medium was inoculated with the resulting culture solution, and subjected to fermentation. The fermentation conditions were as follows: microaerobic conditions (aeration rate of 1 vvm, stirring speed of 200 rpm), 46 g/L of glycerol (500 mM glycerol), pH 7.0, and cultivation temperature of 37° C. While fermenting, ammonia ($NH_3$) was used in order to adjust pH. Samples were taken while fermenting using the recombinant *Klebsiella*. The growth rate was determined by measuring OD600 (optical density) of the sampled specimens. The sampled specimens were subjected to centrifugation at 13,000 rpm for 10 minutes, followed by assaying the concentration of metabolites and 1,3-propanediol in the supernatant by high performance liquid chromatography (HPLC).

As a result, the recombinant strain (Kp ΔldhA) in which ldhA was deleted produced a remarkably reduced amount of lactate which was a major byproduct of the wild type *Klebsiella pneumoniae* (Kp wt). However, the strain produced an increased amount of other byproducts such as formic acid, 2,3-butanediol, ethanol, acetic acid, and succinic acid, which in turn decreased production concentration and production yield of final 1,3-propanediol. In addition, the recombinant strain (KpΔldhA ΔpflB) in which both ldhA and NW were deleted at the same time showed greatly reduced byproducts except 2,3-butanediol while improved production concentration and production yield of 1,3-propanediol as compared to the wild type *Klebsiella pneumoniae* GSC123 (Kp wt) or the ldhA deleted *Klebsiella pneumoniae* Kp ΔldhA. However, concentration of 2,3-butanediol was also greatly increased.

As compared to recombinant strains, namely, Kp ΔldhA ΔpflB ΔbudA or Kp ΔldhA ΔpflB ΔbudC in which a part of enzyme family related to 2,3-butanediol synthesis was deleted, the recombinant strain Kp ΔldhA ΔpflB ΔbudRABC in which the entire operon of 2,3-butanediol was deleted exhibited the highest 1,3-propanediol concentration and the lowest byproduct production. In view of production yield and productivity, the recombinant strain Kp ΔldhA ΔpflB ΔbudRABC showed the best results. Meanwhile, the recombinant strain Kp ΔldhA ΔpflB ΔbudA in which budA was deleted in order to reduce accumulation of 2,3-butanediol and the recombinant strain Kp ΔldhA ΔpflB ΔbudRABC in which budRABC were deleted in order to reduce accumulation of 2,3-butanediol were found to be effective. However, the recombinant strain Kp ΔldhA ΔpflB ΔbudC in which budC was deleted was found to have no effect. The recombinant strain Kp ΔldhA ΔpflB ΔbudA in which budA was deleted showed poor fermentation performance, exhibiting residual glycerol after 24 hours of fermentation which was close to the end point of fermentation. The recombinant strain Kp ΔldhA ΔpflB ΔbudRABC in which budRABC was deleted showed fermentation patterns that were similar to those of parent strain Kp ΔldhA ΔpflB, thereby not producing 2,3-butanediol (Tables 7 and 8, FIGS. 3 to 6).

[Brief Description of the Sequences Provided in the Sequence]

SEQ ID NO: 1 is a nucleotide sequence of ldhA gene. SEQ ID NO: 2 is a homologous region 1 of ldhA gene, and SEQ ID NOs: 3 and 4 are primers for amplification of it. SEQ ID NO: 5 is a homologous region 2 of ldhA gene, and SEQ ID NOs: 6 and 7 are primers for PCR amplification of it. SEQ ID NO: 8 is a DNA fragment in which the homologous regions 1 and 2 of ldhA gene are ligated.

SEQ ID NO: 9 is a nucleotide sequence of pflB gene. SEQ ID NO: 10 is a homologous region 1 of pflB gene, and SEQ ID NOs: 11 and 12 are primers for amplification of it. SEQ ID NO: 13 is a homologous region 2 of pflB gene, and SEQ ID NOs: 14 and 15 are primers for PCR amplification of it. SEQ ID NO: 16 is a DNA fragment in which the homologous regions 1 and 2 of pflB gene are ligated.

SEQ ID NO: 17 is a nucleotide sequence of budA gene. SEQ ID NO: 18 is a homologous region 1 of budA gene, and SEQ ID NOs: 19 and 20 are primers for amplification of it. SEQ ID NO: 21 is a homologous region 2 of budA gene, and

TABLE 7

| Strains | Fermentation products (g/L) | | | | | | |
|---|---|---|---|---|---|---|---|
| | 1,3-propanediol | Lactate | Formic acid | 2,3-butanediol | Ethanol | Acetic acid | Succinic acid |
| Kp wt | 17.3 | 11.5 | 6.1 | 0.0 | 4.7 | 3.8 | 1.8 |
| Kp ΔldhA | 16.3 | 0.4 | 8.4 | 2.6 | 6.2 | 4.6 | 2.4 |
| Kp ΔldhA ΔpflB | 20.0 | 0.3 | 0.0 | 7.0 | 1.4 | 0.4 | 2.2 |
| Kp ΔldhA ΔpflB ΔbudA | 17.7 | 0.0 | 0.7 | 0.0 | 1.5 | 0.2 | 0.1 |
| Kp ΔldhA ΔpflB ΔbudC | 19.4 | 0.7 | 0.0 | 7.9 | 1.2 | 0.1 | 0.9 |
| KpΔldhA ΔpflB ΔbudRABC | 22.1 | 0.3 | 0.0 | 0.0 | 1.7 | 0.1 | 0.0 |

TABLE 8

| Strains | Production result of 1,3-propanediol | | |
|---|---|---|---|
| | Yield (g/g) | Final concentration (g/L) | Productivity (g/L/hr) |
| Kp wt | 0.36 | 17.3 | 1.7 |
| Kp ΔldhA | 0.33 | 16.3 | 1.6 |
| Kp ΔldhA ΔpflB | 0.41 | 20.0 | 1.4 |
| Kp ΔldhA ΔpflB ΔbudA | 0.36 | 17.7 | 0.7 |
| Kp ΔldhA ΔpflB ΔbudC | 0.38 | 19.4 | 0.8 |
| KpΔldhAΔpflB ΔbudRABC | 0.47 | 22.1 | 1.6 |

INDUSTRIAL APPLICABILITY

The present invention relates to a recombinant microorganism for producing 1,3-propanediol, wherein a pathway for converting pyruvate into 2,3-butanediol is suppressed in a microorganism having pyruvate and acetyl-CoA biosynthetic pathways. In addition, the present invention relates to a method for producing 1,3-propanediol using the recombinant microorganism.

SEQ ID NOs: 22 and 23 are primers for PCR amplification of it. SEQ ID NO: 24 is a DNA fragment in which the homologous regions 1 and 2 of budA gene are ligated.

SEQ ID NO: 25 is a nucleotide sequence of budC gene. SEQ ID NO: 26 is a homologous region 1 of budC gene, and SEQ ID NOs: 27 and 28 are primers for amplification of it. SEQ ID NO: 29 is a homologous region 2 of budC gene, and SEQ ID NOs: 30 and 31 are primers for PCR amplification of it. SEQ ID NO: 32 is a DNA fragment in which the homologous regions 1 and 2 of budC gene are ligated.

SEQ ID NO: 33 is a nucleotide sequence of budRABC gene. SEQ ID NO: 34 is a homologous region 1 of budRABC gene, and SEQ ID NOs: 35 and 36 are primers for amplification of it. SEQ ID NO: 37 is a homologous region 2 of budRABC gene, and SEQ ID NOs: 38 and 39 are primers for PCR amplification of it. SEQ ID NO: 40 is a DNA fragment in which the homologous regions 1 and 2 of budRABC gene are ligated.

The invention claimed is:

1. A recombinant *Klebsiella* for producing 1,3-propanediol, wherein
   a pathway for converting pyruvate into α-acetolactate catalyzed by α-acetolactate synthase, a pathway for converting α-acetolactate into acetoin catalyzed by α-acetolactate decarboxylase, a pathway for converting acetoin into 2,3-butanediol catalyzed by acetoin reductase, a pathway for converting pyruvate into lactate catalyzed by lactate dehydrogenase, and a pathway for converting pyruvate into acetyl-CoA catalyzed by pyruvate-formate lyase are suppressed in recombinant *Klebsiella*, and
   the recombinant *Klebsiella* has no ability to produce succinic acid.

2. The recombinant *Klebsiella* for producing 1,3-propanediol according to claim 1, wherein a gene encoding lactate dehydrogenase, a gene encoding pyruvate-formate lyase, a gene encoding transcription activation factor, a gene encoding α-acetolactate decarboxylase, a gene encoding α-acetolactate synthase, and a gene encoding acetoin reductase are suppressed in the recombinant *Klebsiella*.

3. The recombinant *Klebsiella* for producing 1,3-propanediol according to claim 1, wherein a gene having the nucleotide sequence of SEQ ID NO: 1, a gene having the nucleotide sequence of SEQ ID NO: 9 and a gene having the nucleotide sequence of SEQ ID NO: 33 are suppressed in the recombinant *Klebsiella*.

4. The recombinant *Klebsiella* for producing 1,3-propanediol according to claim 1, wherein a pathway for converting pyruvate into formic acid catalyzed by pyruvate-formate lyase is further suppressed.

5. A method for producing 1,3-propanediol, comprising:
   growing the recombinant *Klebsiella* according to claim 1 in a culture medium; and
   harvesting 1,3-propanediol from the culture medium.

6. A recombinant *Klebsiella* for producing 1,3-propanediol, wherein a gene having the nucleotide sequence of SEQ ID NO: 1, a gene having the nucleotide sequence of SEQ ID NO: 9 and a gene having the nucleotide sequence of SEQ ID NO: 33 are suppressed in the recombinant *Klebsiella*.

7. The recombinant *Klebsiella* for producing 1,3-propanediol according to claim 6, wherein the recombinant *Klebsiella* has no ability to produce succinic acid.

8. A recombinant *Klebsiella* for producing 1,3-propanediol, wherein a gene encoding lactate dehydrogenase, a gene encoding pyruvate-formate lyase, a gene encoding transcription activation factor, a gene encoding α-acetolactate decarboxylase, a gene encoding α-acetolactate synthase, and a gene encoding acetoin reductase are suppressed in the recombinant *Klebsiella*.

9. The recombinant *Klebsiella* for producing 1,3-propanediol according to claim 8, wherein the recombinant *Klebsiella* has no ability to produce succinic acid.

* * * * *

SEQUENCE LISTING

<160> NUMBER OF SEQ ID NOS: 40

<210> SEQ ID NO 1
<211> LENGTH: 987
<212> TYPE: DNA
<213> ORGANISM: Klebsiella pneumoniae

<400> SEQUENCE: 1

| | | | | | |
|---|---|---|---|---|---|
| atgaaaatcg | cggtttatag | tacgaagcag | tacgataaaa | agtacctgca | gcacgttaat | 60 |
| gatgcatacg | gctttgaact | ggaattcttc | gatttcctgc | tgacagcgaa | gactgccaaa | 120 |
| accgccaacg | gttgcgaagc | ggtatgtatc | ttcgtcaatg | acgacggcag | ccgcccggtg | 180 |
| ctggaagagc | tgaaggccca | cggggtgaaa | tatatcgccc | tgcgctgcgc | cgggtttaac | 240 |
| aacgtcgacc | ttgaggcggc | aaaggagctt | ggcctgcgcg | tcgtgcgcgt | tccagcttac | 300 |
| tctccggaag | cggtcgctga | gcatgcgatc | ggtatgatga | tgtcgctcaa | ccgccgcatc | 360 |
| caccgcgctt | accagcgtac | ccgcgatgcc | aatttctccc | tcgaaggcct | caccggcttc | 420 |
| accatgtacg | gcaaaaccgc | cggggtgatc | ggcaccggga | aaattggcgt | agcgatgttg | 480 |
| cggatcctca | aaggcttcgg | catgcgcctg | ctggcgttcg | acccgtaccc | aagcgccgcc | 540 |
| gcgctggagc | tgggggtgga | atatgttgac | ctcgccacgc | tgtacaagga | atcggacgtg | 600 |
| atctccctgc | actgtccgct | gaccgacgaa | aactaccacc | tgctcaatcg | cgaagctttc | 660 |
| gatcagatga | agacggggt | gatggtgatc | aacaccaccc | gcggcgccct | gatcgactct | 720 |
| caggcggcca | tcgacgccct | gaagcaccag | aaaattggcg | cgctggggct | ggacgtttat | 780 |
| gagaacgaac | gcgatctgtt | ctttgaagac | aaatccaacg | acgtgatcca | ggacgatgtc | 840 |
| ttccgccgcc | tctccgcctg | ccataacgtg | ctgtttaccg | gccaccaggc | gttcctcacc | 900 |
| gccgaggcgc | tgatcagcat | tcggagacc | actctgggta | acctgcagca | ggtcgccaac | 960 |
| ggcgaaacct | gtccgaacgc | catcgtc | | | | 987 |

<210> SEQ ID NO 2
<211> LENGTH: 1200
<212> TYPE: DNA
<213> ORGANISM: Artificial
<220> FEATURE:
<223> OTHER INFORMATION: a homologous region 1 of ldhA gene

<400> SEQUENCE: 2

| | | | | | |
|---|---|---|---|---|---|
| caagcgtgcg | cggtgaaccg | ggagagggat | cgctggccgg | cagtttgctc | aggcaggcgc | 60 |
| tgttgatctc | cagctggcca | atatgcagcc | gccagcggct | gggacgcgag | agacgggcat | 120 |
| cggtcacccg | ggcgatttca | cagtcgccca | ccagataacg | cagatcgggg | atcagcaggg | 180 |
| ccgaccgcgt | caggcgcggg | ctctcctgca | aagagatacg | cgtgcccacg | ggcagccaga | 240 |
| tgcccgccag | cgtcggcacc | cagtgggtta | gcgtcaacag | cagggttagc | ggcaataaca | 300 |
| ccagaactaa | caccagcgcg | atggcggctt | tatatttacc | cttcatgggc | agttaatatc | 360 |
| ctgattcaac | ataagtaaaa | gccgaaaggc | gtccattgtg | acacgttcga | ccagtgagtg | 420 |
| aaagtttacg | gcctgttaaa | gcatagttgc | cagccggact | cgcggcgcga | cgttcggcca | 480 |
| ttatcattta | actgttgttt | aagtcgcccc | tgccacactc | cagccagacg | ggaatagctt | 540 |
| gcgggagagg | cggtgtcgtt | aattatctcg | ctcatagaga | gcgcacagga | ccactatcca | 600 |
| tgggtattgc | tgattgtttt | tctgcttacc | ttcactaaat | cctgcgcatt | ggtctcgctg | 660 |
| gcaatccccg | gcacctccgg | cctgctgctg | ctggggacat | tcgcttccgc | cagcctcgga | 720 |
| catttcctgt | taatgtggtc | cagcgccagc | ctcggcgcca | tcggcggatt | ctggctatcg | 780 |

```
tggcggctgg gcattcgcta ccgtcatcgc ctcacccatc tacgctggct gaccgccgag      840
cgtctggccc gcagccgcct cttctttcag cgctatggcc cgtgggctat cttttcagc       900 cgctttctct ctcccctgag ggctacgctg cccttcgtta gcggcgccag cagtctgccg      960
ctgtggtcgt ttcagctggc taacgtcagc tccggtctgc tgtggccgct tctgctgctc     1020
gcccccggcg ctttcagcct cagtttgtgg tgaaaaaact ttgtctttca aagagattcc     1080
gcaagtccgc gatatgctct agaattagga ttagcaccct ctcattaaac tatttttaa      1140 taattgtacg attattttaa atatgctacc gtgacggtat aatcactgga gaaaagtctt    1200
```

<210> SEQ ID NO 3
<211> LENGTH: 30
<212> TYPE: DNA
<213> ORGANISM: Artificial
<220> FEATURE:
<223> OTHER INFORMATION: a primer for amplification of the sequence of
      SEQ ID NO: 2

<400> SEQUENCE: 3

```
tagaggatcc caagcgtgcg cggtgaaccg                                        30
```

<210> SEQ ID NO 4
<211> LENGTH: 47
<212> TYPE: DNA
<213> ORGANISM: Artificial
<220> FEATURE:
<223> OTHER INFORMATION: a primer for amplification of the sequence of
      SEQ ID NO: 2

<400> SEQUENCE: 4

```
gaggagcaca aagggaaag gcgaagactt ttctccagtg attatac                      47
```

<210> SEQ ID NO 5
<211> LENGTH: 1199
<212> TYPE: DNA
<213> ORGANISM: Artificial
<220> FEATURE:
<223> OTHER INFORMATION: a homologous region 2 of ldhA gene

<400> SEQUENCE: 5

```
cgcctttccc ttttgtgctc ctctcccggg gggagcacat tcagataatc cccacagatc       60
cctgctgcga taccgttaca ctggcttggt tttattagtt atatgattgt tttggagtga      120
aaatgaacaa atttgcggcg cttctggcgg caggtatgct gctgtccggc tgtgtctata     180
atagtaaggt gtccaccggt gcggaacagc tgcagcatca tcgtttcgtg ctgaccagcg      240
tcaacggcca ggcggtcaac gccagcgacc ggccgctgga gctgagcttc ggtgagaaga      300
tggctattac cggcaagatg tatgtatccg gcaatatgtg caacggcttt agcggggaag      360
gtaaagtgtc ggacggcgag ctgaaggtca atcgctggc gatgacccgg atgctgtgcc       420
acgacgccca gctcaatacc ctggatgcga cgatcgacaa gatgctgcgc gagggtgcgc      480
aggtcgatct gacggaaaac cagttgacgc tggcgaccgc cgaccagacg ctggtctata      540
agctcgccga cctgatgcac tagccggcgt tgaggtgccg ctgacgctgc cccgcgacgg      600
ggccgctgtt agtagccgca gctgccaccc gccagcgcct gctcgctgca gcgtttgccg      660
ttcggcagcg cgcacatgcc aatcgccgaa ccatcgagct gacgagccac cgataacgag      720
ccgcctatca tggcgcagtt ggcctgaccg gcgtcgctca tcgccgcccg cattcccggc      780
gtgacgtgcg ccgccgtggc ctgctgaacg ggttcactac tgcacgcgga cagcaacagc      840
```

```
gccgcacatc ctactaacat cgcagctcgc attctctctc ccctcggaaa cgtcttaaaa    900
aagcaaaccc cagaataata ggcagcgtgg cgggcggcgt cgagagggga agtacgtatt    960
tatgcgcctc attaacattt tctagcaaat tttcgcctaa agcttgatct gcctcggcca   1020
tgtcgcccgg cgcaggtggt tcatctcccg gcaggcagcc attttctccg cgaaccacgc   1080
aaaatattga tctggtcacg ggtacccggc gcattgagga cacaaatgca aaaatggcgg   1140
ggtcagcggt ttgctaaact accccttata taattacagg gcgcgtcgcg gtttcacgc    1199
```

```
<210> SEQ ID NO 6
<211> LENGTH: 47
<212> TYPE: DNA
<213> ORGANISM: Artificial
<220> FEATURE:
<223> OTHER INFORMATION: a primer for amplification of the sequence of
      SEQ ID NO: 5

<400> SEQUENCE: 6
gtataatcac tggagaaaag tcttcgcctt tcccttttgt gctcctc                   47

<210> SEQ ID NO 7
<211> LENGTH: 31
<212> TYPE: DNA
<213> ORGANISM: Artificial
<220> FEATURE:
<223> OTHER INFORMATION: a primer for amplification of the sequence of
      SEQ ID NO: 5

<400> SEQUENCE: 7
atcgcggccg cgcgtgaaac cgcgacgcgc c                                    31

<210> SEQ ID NO 8
<211> LENGTH: 2399
<212> TYPE: DNA
<213> ORGANISM: Artificial
<220> FEATURE:
<223> OTHER INFORMATION: a DNA fragment in which the homologous regions
      1 and 2 of ldhA gene are ligated

<400> SEQUENCE: 8
caagcgtgcg cggtgaaccg ggagagggat cgctggccgg cagtttgctc aggcaggcgc     60
tgttgatctc cagctggcca atatgcagcc gccagcggct gggacgcgag agacgggcat    120
cggtcacccg ggcgatttca cagtcgccca ccagataacg cagatcgggg atcagcaggg    180
ccgaccgcgt caggcgcggg ctctcctgca aagagatacg cgtgcccacg ggcagccaga    240
tgcccgccag cgtcggcacc cagtgggtta gcgtcaacag caggggttagc ggcaataaca    300 ccagaactaa caccagcgcg atggcggctt tatatttacc cttcatgggc agttaatatc    360
ctgattcaac ataagtaaaa gccgaaaggc gtccattgtg acacgttcga ccagtgagtg    420
aaagtttacg gcctgttaaa gcatagttgc cagccggact cgcggcgcga cgttcggcca    480
ttatcattta actgttgttt aagtcgcccc tgccacactc cagccagacg gaatagctt    540 gcgggagagg cggtgtcgtt aattatctcg ctcatagaga gcgcacagga ccactatcca    600
tgggtattgc tgattgtttt tctgcttacc ttcactaaat cctgcgcatt ggtctcgctg    660
gcaatccccg gcacctccgg cctgctgctg ctggggacat tcgcttccgc cagcctcgga    720
catttcctgt taatgtggtc cagcgccagc ctcggcgcca tcgcggatt ctggctatcg    780 tggcggctgg gcattcgcta ccgtcatcgc ctcacccatc tacgctggct gaccgccgag    840
cgtctggccc gcagccgcct cttctttcag cgctatggcc gtgggctat cttttttcagc    900
```

```
cgctttctct ctcccctgag ggctacgctg cccttcgtta gcggcgccag cagtctgccg    960
ctgtggtcgt ttcagctggc taacgtcagc tccggtctgc tgtggccgct tctgctgctc   1020
gcccccggcg ctttcagcct cagtttgtgg tgaaaaaact ttgtctttca aagagattcc   1080
gcaagtccgc gatatgctct agaattagga ttagcaccct ctcattaaac tatttttaa    1140 taattgtacg attattttaa atatgctacc gtgacggtat aatcactgga gaaaagtctt   1200
cgcctttccc ttttgtgctc ctctcccggg gggagcacat tcagataatc cccacagatc   1260
cctgctgcga taccgttaca ctggcttggt tttattagtt atatgattgt tttggagtga   1320
aaatgaacaa atttgcggcg cttctggcgg caggtatgct gctgtccggc tgtgtctata   1380
atagtaaggt gtccaccggt gcggaacagc tgcagcatca tcgtttcgtg ctgaccagcg   1440
tcaacggcca gcggtcaac gccagcgacc ggccgctgga gctgagcttc ggtgagaaga   1500
tggctattac cggcaagatg tatgtatccg gcaatatgtg caacggcttt agcggggaag   1560
gtaaagtgtc ggacggcgag ctgaaggtca atcgctggc gatgacccgg atgctgtgcc   1620
acgacgccca gctcaatacc ctggatgcga cgatcgacaa gatgctgcgc gagggtgcgc   1680
aggtcgatct gacggaaaac cagttgacgc tggcgaccgc cgaccagacg ctggtctata   1740
agctcgccga cctgatgcac tagccggcgt tgaggtgccg ctgacgctgc cccgcgacgg   1800
ggccgctgtt agtagccgca gctgccaccc gccagcgcct gctcgctgca gcgtttgccg   1860
ttcggcagcg cgcacatgcc aatcgccgaa ccatcgagct gacgagccac cgataacgag   1920
ccgcctatca tggcgcagtt ggcctgaccg gcgtcgctca tcgccgcccg cattcccggc   1980
gtgacgtgcg ccgccgtggc ctgctgaacg ggttcactac tgcacgcgga cagcaacagc   2040
gccgcacatc ctactaacat cgcagctcgc attctctctc ccctcggaaa cgtcttaaaa   2100
aagcaaaccc cagaataata ggcagcgtgg cgggcggcgt cgagagggga agtacgtatt   2160
tatgcgcctc attaacattt tctagcaaat tttcgcctaa agcttgatct gcctcggcca   2220
tgtcgcccgg cgcaggtggt tcatctcccg gcaggcagcc attttctccg cgaaccacgc   2280
aaaatattga tctggtcacg ggtacccggc gcattgagga cacaaatgca aaaatggcgg   2340
ggtcagcggt ttgctaaact accccttata taattacagg gcgcgtcgcg gtttcacgc    2399
```

<210> SEQ ID NO 9
<211> LENGTH: 2280
<212> TYPE: DNA
<213> ORGANISM: Klebsiella pneumoniae

<400> SEQUENCE: 9

```
atgtccgagc ttaatgaaaa gttagccaca gcctgggaag gttttgcgaa aggtgactgg     60
cagaatgaag tcaacgtccg tgactttatt cagaaaaact acaccccata tgaaggcgac    120
gaatccttcc tggctggcgc gactgaagcg accaccaagc tgtgggacac cgtaatggaa    180
ggtgtaaaac aggaaaaccg cactcacgcg cctgttgatt ttgacactgc cctggcttcc    240 accatcaccct ctcacgacgc gggctatatc gagaaaggtc tggaaaaaat cgttggtctg    300
cagaccgaag cgccgctgaa acgtgcgatc atcccgttcg gtggtatcaa aatggttgaa    360
ggttcctgca agcgtataa tcgcgagctg gacccgatgc tgaaaaaaat cttcacagag    420
taccgtaaaa ctcacaacca gggcgttttc gacgtctata cccggacat tctgcgctgc    480 cgtaaatccg gcgtgctgac gggtctgccg gatgcttacg gtcgtggtcg tatcatcggt    540
gactaccgtc gcgttgcgct gtacggtatc gacttcctga tgaaagacaa attcgcccag    600
ttcaactctc tgcaagcgaa actggaaagc ggcgaagacc tggaagcgac catccgtctg    660
```

```
cgtgaagaaa tcgctgaaca acaccgcgca ctgggccaga tcaaagagat ggccgctaaa    720
tatggctatg acatctccgg tccggcgacc accgctcagg aagcgattca gtggacctac    780
ttcggttacc tggctgccgt gaaatctcag aacggcgcgg caatgtcctt cggtcgtacc    840
tccagcttcc tggatatcta catcgagcgt gacctgcagg cgggtaaaat caccgagcaa    900
gacgcgcagg aaatggttga ccacctggtc atgaaactgc gtatggttcg cttcctgcgt    960
accccggaat atgatgaact gttctccggc gacccgattt gggcaacgga atccatcggc   1020
ggtatgggcg ttgacggccg tactctggtg accaaaaaca gcttccgctt cctgaacacc   1080
ctgtacacca tggggccgtc tccggagccg aacattacta tcctgtggtc tgaaaaactg   1140
ccgctgagct tcaagaaatt cgccgctaaa gtgtccatcg atacctcttc tctgcagtat   1200
gagaacgatg acctgatgcg tccggacttc aacaacgacg actacgctat cgcatgctgc   1260
gtaagcccga tggttgttgg taagcaaatg cagttcttcg gcgctcgcgc taacctcgcg   1320
aaaaccatgc tgtacgctat caacggcggc gtggatgaaa aactgaaaat gcaggttggt   1380
ccgaaatctg aaccgatcaa aggcgacgtc ctgaacttcg acgaagtaat ggatcgcatg   1440
gatcacttca tggactggct ggctaaacag tacgtcaccg cgctgaacat catccactac   1500
atgcacgaca agtacagcta cgaagcctct ctgatggcgc tgcacgaccg tgacgttatc   1560
cgcaccatgg cgtgtggtat cgctggtctg tccgttgctg ctgactccct gtctgctatc   1620
aaatatgcga agttaaaacc gattcgtgac gaagacggtc tggctatcga cttcgaaatc   1680
gaaggcgaat acccgcagtt tggtaacaac gaccctcgcg tcgatgacat ggccgttgac   1740
ctggttgaac gtttcatgaa gaaaattcag aaactgcaca cctaccgcaa cgctatcccg   1800
actcagtctg ttctgaccat cacctctaac gtggtgtacg gtaagaaaac cggtaatacc   1860
ccagacggtc gtcgcgctgg cgcgccgttc ggtccaggtg ctaacccgat gcacggccgt   1920
gaccagaaag cgcagtagc ctctctgacc tccgtcgcta aactgccgtt tgcttacgcg   1980
aaagatggta tctcttatac cttctctatc gtgccgaacg cgctgggtaa agacgacgaa   2040
gttcgtaaga ccaacctggc gggtctgatg gatggttact ccatcacgaa gcgtccatc   2100 gaaggtggtc agcacctgaa cgtgaacgtc atgaaccgcg aaatgctgct cgacgcgatg   2160
gaaaacccgg aaaaatatcc gcagctgacc atccgtgtat ctggctacgc cgtacgtttt   2220
aactccctga ccaaagaaca gcagcaggat gttattaccc gtaccttcac tcagaccatg   2280
```

<210> SEQ ID NO 10
<211> LENGTH: 529
<212> TYPE: DNA
<213> ORGANISM: Artificial
<220> FEATURE:
<223> OTHER INFORMATION: a homologous region 1 of pflB gene

<400> SEQUENCE: 10

```
gtttgtgctg ctgatgtggt tatcaggcga atatatgact gccaacggcg gctgggggct     60
aaacgttctg cagaccgccg accacaaaat gcaccatact tttgtggagg ccgtgagcct    120
gggtatcctc gctaacctga tggtttgtct cgccgtatgg atgagctatt ccggtcgtag    180
cctgatggat aaagcgatga tcatggtcct gccggtagca atgttcgttg ccagcggctt    240
tgagcacagc atcgccaaca tgtttatgat cccgatgggt atcgtaatcc gcaactttgc    300
aagcccggaa ttctggaccg ccatcggttc gactccggaa agtttctctc acttgaccgt    360
tatgaacttc atcactgata acctgattcc ggtaactatc gggaacatta tcggcggggg    420
```

```
tctgctggtc gggttgacat actgggtcat ttacctgcgt ggcaacgacc atcactaagg      480
gttgtttcag gcagtaaata aaaaatccac ttaagaaggt aggtgttac                  529
```

<210> SEQ ID NO 11
<211> LENGTH: 34
<212> TYPE: DNA
<213> ORGANISM: Artificial
<220> FEATURE:
<223> OTHER INFORMATION: a primer for amplification of the sequence of
      SEQ ID NO: 10

<400> SEQUENCE: 11

```
ggatccgttt gtgctgctga tgtggttatc aggc                                  34
```

<210> SEQ ID NO 12
<211> LENGTH: 46
<212> TYPE: DNA
<213> ORGANISM: Artificial
<220> FEATURE:
<223> OTHER INFORMATION: a primer for amplification of the sequence of
      SEQ ID NO: 10

<400> SEQUENCE: 12

```
cgccttttca gtcagacagg gaagtaacac ctaccttctt aagtgg                     46
```

<210> SEQ ID NO 13
<211> LENGTH: 596
<212> TYPE: DNA
<213> ORGANISM: Artificial
<220> FEATURE:
<223> OTHER INFORMATION: a homologous region 2 of pflB gene

<400> SEQUENCE: 13

```
ttccctgtct gactgaaaag gcgtacaata aaggccccac atcagtgggg cctttttaac      60
aagcattccc cgccccagcc tgctttgcca gttatctata ctttgggtac ctgtcaaaac     120
agactcgacg cagccgctga gctgcgcacc aacacggccc cggatgggcc acatctggag     180
aaaacaccgc aatgtcagtt attggtcgca ttcactcctt tgaatcctgt ggcaccgttg     240
atggcccagg catccgcttt attacctttt tccagggctg cctgatgcgc tgcctgtact     300
gccataaccg tgacacctgg gatacccacg gcggcaaaga aatcaccgtt gaagaattaa     360
tgaaagaggt ggtgacctat cgtcacttta tgaatgcttc cggcggcggc gtcaccgcct     420
cgggcggtga ggcgatcctg caggcggagt tgttcgcga ctggttccgc gcgtgtaaga      480
aagaaggcat ccacacctgc ctggatacca acgcttcgt acgtcgctac gatccggtta      540
tcgacgagct gctggaggta acagacctgg tgatgctgga tctcaagcag atgaac         596
```

<210> SEQ ID NO 14
<211> LENGTH: 46
<212> TYPE: DNA
<213> ORGANISM: Artificial
<220> FEATURE:
<223> OTHER INFORMATION: a primer for amplification of the sequence of
      SEQ ID NO: 13

<400> SEQUENCE: 14

```
ccacttaaga aggtaggtgt tacttccctg tctgactgaa aaggcg                     46
```

<210> SEQ ID NO 15
<211> LENGTH: 36
<212> TYPE: DNA
<213> ORGANISM: Artificial
<220> FEATURE:

<223> OTHER INFORMATION: a primer for amplification of the sequence of
       SEQ ID NO: 13

<400> SEQUENCE: 15
gcggccgcgt tcatctgctt gagatccagc atcacc                              36

<210> SEQ ID NO 16
<211> LENGTH: 1125
<212> TYPE: DNA
<213> ORGANISM: Artificial
<220> FEATURE:
<223> OTHER INFORMATION: a DNA fragment in which the homologous regions
       1 and 2 of pflB gene are ligated

<400> SEQUENCE: 16
gtttgtgctg ctgatgtggt tatcaggcga atatatgact gccaacggcg gctgggggct      60
aaacgttctg cagaccgccg accacaaaat gcaccatact tttgtggagg ccgtgagcct     120
gggtatcctc gctaacctga tggtttgtct cgccgtatgg atgagctatt ccggtcgtag     180
cctgatggat aaagcgatga tcatggtcct gccggtagca atgttcgttg ccagcggctt     240
tgagcacagc atcgccaaca tgtttatgat cccgatgggt atcgtaatcc gcaactttgc     300
aagcccggaa ttctggaccg ccatcggttc gactccggaa agtttctctc acttgaccgt     360
tatgaacttc atcactgata acctgattcc ggtaactatc gggaacatta tcggcggggg     420
tctgctggtc gggttgacat actgggtcat ttacctgcgt ggcaacgacc atcactaagg     480
gttgtttcag gcagtaaata aaaaatccac ttaagaaggt aggtgttact tccctgtctg     540
actgaaaagg cgtacaataa aggccccaca tcagtgggc cttttttaaca agcattcccc     600 gccccagcct gctttgccag ttatctatac tttgggtacc tgtcaaaaca gactcgacgc     660
agccgctgag ctgcgcacca cacggcccc ggatgggcca catctggaga aaacaccgca     720
atgtcagtta ttggtcgcat tcactccttt gaatcctgtg gcaccgttga tggcccaggc     780
atccgcttta ttacctttt ccagggctgc ctgatgcgct gcctgtactg ccataaccgt     840
gacacctggg ataccacacgg cggcaaagaa atcaccgttg aagaattaat gaaagaggtg     900
gtgacctatc gtcactttat gaatgcttcc ggcggcggcg tcaccgcctc gggcggtgag     960
gcgatcctgc aggcggagtt tgttcgcgac tggttccgcg cgtgtaagaa agaaggcatc    1020
cacacctgcc tggataccaa cggcttcgta cgtcgctacg atccggttat cgacgagctg    1080
ctggaggtaa cagacctggt gatgctggat ctcaagcaga tgaac                    1125

<210> SEQ ID NO 17
<211> LENGTH: 777
<212> TYPE: DNA
<213> ORGANISM: Klebsiella pneumoniae

<400> SEQUENCE: 17
atgaatcatt ctgctgaatg cacctgcgaa gagagtctat gcgaaaccct gcgggcgttt      60
tccgcgcagc atcccgagag cgtgctctat cagacatcgc tcatgagcgc cctgctgagc     120
ggggtttacg aaggcagcac caccatcgcc gacctgctga acacggcga tttcggcctc     180 ggcacccttta atgagctgga cggggagctg atcgccttca gcagtcaggt ctatcagctg     240
cgcgccgacg gcagcgcgcg caaagcccag ccggagcaga aaacgccgtt cgcggtgatg     300
acctggttcc agccgcagta ccggaaaacc tttgaccatc cggtgagccg ccagcagctg     360
cacgaggtga tcgaccagca aatcccctct gacaacctgt tctgcgccct gcgcatcgac     420
ggccatttcc gccatgccca tacccgcacc gtgccgcgcc agacgccgcc gtaccgggcg     480

```
atgaccgacg tactcgacga tcagccggtg ttccgcttta accagcgcga agggtgctg      540 gtcggcttcc ggaccccgca gcatatgcag gggatcaacg tcgccgggta tcacgagcat     600
tttattaccg atgaccgcaa aggcggcggt cacctgctgg attaccagct cgaccacggg     660
gtgctgacct tcggcgaaat tcacaagctg atgatcgacc tgcccgccga cagcgcgttc    720
ctgcaggcta atctgcatcc cgataatctc gatgccgcca tccgttccgt agaaagt       777
```

```
<210> SEQ ID NO 18
<211> LENGTH: 653
<212> TYPE: DNA
<213> ORGANISM: Artificial
<220> FEATURE:
<223> OTHER INFORMATION: a homologous region 1 of budA gene

<400> SEQUENCE: 18
```

```
gcagattaaa ggctttactg ctctcgcacg gcaggcggac gaaggcgata tccagctcgg     60
cctcgctcag ggcggtcatc agattggcca tattgtcttc catctggtgc agggtcaccc    120
cggggtggtc gagctgaaaa cggtgcagca gcgtgaagat ttgcggatgg aaagcatcag    180
aactggtaat gcctagcgac aggctgccgt tcatcccgcg cgcaatgccc ttggccttct    240
ccagcgccgc atcgctcatg gcgaggatct ggcgggcatc ctcatagaaa gactctcccg    300
cttccgtcag ctccaccccg cgggttaaac gccggaacag cggggtcccc acctcgcgct    360
caagccgctg aatttgctga cttaacggag gctgtgaaat acccagctcc ttggcggcct    420
gggtgaagtg ccgcgtcctg gcgacggcga caaaatagcg aagataacga agttccatat    480
cgaaaacgtc tcaaaccagc atggtttcta tattggaact gtgagctgaa tcgggtcaac    540
atttatttaa cctttcttat atttgttgaa cgaggaagtg gtatatgaat cattctgctg    600
aatgcacctg cgaacccgat aatctcgatg ccgccatccg ttccgtagaa agt           653
```

```
<210> SEQ ID NO 19
<211> LENGTH: 37
<212> TYPE: DNA
<213> ORGANISM: Artificial
<220> FEATURE:
<223> OTHER INFORMATION: a primer for amplification of the sequence of
      SEQ ID NO: 18

<400> SEQUENCE: 19
tctagaggat ccgcagatta aaggctttac tgctctc                              37
```

```
<210> SEQ ID NO 20
<211> LENGTH: 54
<212> TYPE: DNA
<213> ORGANISM: Artificial
<220> FEATURE:
<223> OTHER INFORMATION: a primer for amplification of the sequence of
      SEQ ID NO: 18

<400> SEQUENCE: 20
cggatggcgg catcgagatt atcgggttcg caggtgcatt cagcagaatg attc           54
```

```
<210> SEQ ID NO 21
<211> LENGTH: 601
<212> TYPE: DNA
<213> ORGANISM: Artificial
<220> FEATURE:
<223> OTHER INFORMATION: a homologous region 2 of budA gene

<400> SEQUENCE: 21
```

```
atgaatcatt ctgctgaatg cacctgcgaa cccgataatc tcgatgccgc catccgttcc    60
gtagaaagtt aagggggtca catggacaaa cagtatccgg tacgccagtg ggcgcacggc   120
gccgatctcg tcgtcagtca gctggaagca caggggtac gccaggtgtt cggcatcccc   180
ggcgccaaaa tcgacaaggt cttcgattca ctgctggatt cctccattcg cattattccg   240
gtacgccacg aagccaacgc cgcatttatg gccgccgccg tcggacgtat taccggcaaa   300
gcgggcgtgg cgctggtcac ctccggtccg ggttgttcta acctgatcac cggcatggcc   360
accgcgaaca gcgaaggcga cccggtggtg gccctgggcg gcgcggtaaa acgcgccgat   420
aaagccaaac aggtccacca gagtatggat acggtggcga tgttcagccc ggtcaccaaa   480
tacgccgtcg aggtgacggc gccggatgcg ctggcggaag tggtctccaa cgccttccgc   540
gccgccgagc agggccggcc gggcagcgcg ttcgttagcc tgccgcagga tgtggtcgat   600
g                                                                  601

<210> SEQ ID NO 22
<211> LENGTH: 54
<212> TYPE: DNA
<213> ORGANISM: Artificial
<220> FEATURE:
<223> OTHER INFORMATION: a primer for amplification of the sequence of
      SEQ ID NO: 21

<400> SEQUENCE: 22
gaatcattct gctgaatgca cctgcgaacc cgataatctc gatgccgcca tccg           54

<210> SEQ ID NO 23
<211> LENGTH: 35
<212> TYPE: DNA
<213> ORGANISM: Artificial
<220> FEATURE:
<223> OTHER INFORMATION: a primer for amplification of the sequence of
      SEQ ID NO: 21

<400> SEQUENCE: 23
gatcgcggcc gccatcgacc acatcctgcg gcagg                                35

<210> SEQ ID NO 24
<211> LENGTH: 1185
<212> TYPE: DNA
<213> ORGANISM: Artificial
<220> FEATURE:
<223> OTHER INFORMATION: a DNA fragment in which the homologous regions
      1 and 2 of budA gene are ligated

<400> SEQUENCE: 24
gcagattaaa ggctttactg ctctcgcacg gcaggcggac gaaggcgata tccagctcgg    60
cctcgctcag ggcggtcatc agattggcca tattgtcttc catctggtgc agggtcaccc   120
cggggtggtc gagctgaaaa cggtgcagca gcgtgaagat ttgcggatgg aaagcatcag   180
aactggtaat gcctagcgac aggctgccgt tcatcccgcg cgcaatgccc ttggccttct   240
ccagcgccgc atcgctcatg gcgaggatct ggcgggcatc ctcatagaaa gactctcccg   300
cttccgtcag ctccaccccg cggggttaaac gccggaacag cggggtcccc acctcgcgct   360
caagccgctg aatttgctga cttaacggag gctgtgaaat acccagctcc ttggcggcct   420
gggtgaagtg ccgcgtcctg gcgacggcga caaaatagcg aagataacga agttccatat   480
cgaaaacgtc tcaaaccagc atggtttcta tattggaact gtgagctgaa tcgggtcaac   540
atttatttaa ccttttcttat atttgttgaa cgaggaagtg gtatatgaat cattctgctg   600
```

| | |
|---|---|
| aatgcacctg cgaacccgat aatctcgatg ccgccatccg ttccgtagaa agttaagggg | 660 |
| gtcacatgga caaacagtat ccggtacgcc agtgggcgca cggcgccgat ctcgtcgtca | 720 |
| gtcagctgga agcacagggg gtacgccagg tgttcggcat ccccggcgcc aaaatcgaca | 780 |
| aggtcttcga ttcactgctg gattcctcca ttcgcattat tccggtacgc cacgaagcca | 840 |
| acgccgcatt tatggccgcc gccgtcggac gtattaccgg caaagcgggc gtggcgctgg | 900 |
| tcacctccgg tccgggttgt tctaacctga tcaccggcat ggccaccgcg aacagcgaag | 960 |
| gcgacccggt ggtggccctg gcggcgcgg taaaacgcgc cgataaagcc aaacaggtcc | 1020 |
| accagagtat ggatacggtg gcgatgttca gcccggtcac caaatacgcc gtcgaggtga | 1080 |
| cggcgccgga tgcgctggcg gaagtggtct ccaacgcctt ccgcgccgcc gagcagggcc | 1140 |
| ggccgggcag cgcgttcgtt agcctgccgc aggatgtggt cgatg | 1185 |

<210> SEQ ID NO 25
<211> LENGTH: 768
<212> TYPE: DNA
<213> ORGANISM: Klebsiella pneumoniae

<400> SEQUENCE: 25

| | |
|---|---|
| atgaaaaaag tcgcacttgt taccggcgcc ggccagggga ttggtaaagc tatcgccctt | 60 |
| cgtctggtga aggatggatt tgccgtggcc attgccgatt ataacgacgc caccgccaaa | 120 |
| gcggtcgcct ccgaaatcaa ccaggccggc ggccgcgcca tggcggtgaa agtggatgtt | 180 |
| tctgaccgcg accaggtatt tgccgccgtc gaacaggcgc gcaaaacgct gggcggcttc | 240 |
| gacgtcatcg tcaacaacgc cggcgtggcg ccatccacgc cgatcgagtc cattaccccg | 300 |
| gagattgtcg acaaagtcta caacatcaac gtcaaggggg tgatctgggg catccaggca | 360 |
| gcggtcgagg cctttaagaa agagggtcac ggcgggaaaa tcatcaacgc ctgttcccag | 420 |
| gccggccacg tcggcaaccc ggagctggcg gtatatagct cgagtaaatt cgcggtacgc | 480 |
| ggcttaaccc agaccgccgc tcgcgacctc gcgccgctgg catcaccggt caacggctac | 540 |
| tgcccgggga ttgtcaaaac gccgatgtgg gccgaaattg accgccaggt gtccgaagcc | 600 |
| gccggtaaac cgctgggcta cggtaccgcc gagttcgcca aacgcatcac cctcggccgc | 660 |
| ctgtccgagc cggaagatgt cgccgcctgc gtctcctatc ttgccagccc ggattctgat | 720 |
| tatatgaccg tcagtcatt gctgatcgac ggcggcatgg tgtttaac | 768 |

<210> SEQ ID NO 26
<211> LENGTH: 640
<212> TYPE: DNA
<213> ORGANISM: Artificial
<220> FEATURE:
<223> OTHER INFORMATION: a homologous region 1 of budC gene

<400> SEQUENCE: 26

| | |
|---|---|
| gctgcgtatc gttcgcgcca tgcaggacat cgtcaacagc gacgtcacgt tgaccgtgga | 60 |
| catgggcagc ttccatatct ggattgcccg ctacctgtac agcttccgcg cccgccaggt | 120 |
| gatgatctcc aacggccagc agaccatggg cgtcgccctg ccctgggcca tcggcgcctg | 180 |
| gctggtcaat cctgagcgca agtggtctc cgtctccggc gacggcggct tcctgcagtc | 240 |
| gagcatggag ctggagaccg ccgtccgcct gaaagccaac gtgctgcacc tgatctgggt | 300 |
| cgataacggc tacaacatgg tggccattca ggaagagaaa aaataccagc gcctgtccgg | 360 |
| cgtcgagttt gggccgatgg attttaaagc ctatgccgaa tccttcggcg cgaaagggtt | 420 |
| tgccgtggaa agcgccgagg cgctggagcc gaccctgcgc gcggcgatgg acgtcgacgg | 480 |

```
cccggcggta gtggccatcc cggtggatta tcgcgataac ccgctgctga tgggccagct    540
gcatctgagt cagattctgt aagtcatcac aataaggaaa gaaaaatgaa aaaagtcgca    600
cttgttaccg gcgccatgac cggtcagtca ttgctgatcg                          640
```

<210> SEQ ID NO 27
<211> LENGTH: 35
<212> TYPE: DNA
<213> ORGANISM: Artificial
<220> FEATURE:
<223> OTHER INFORMATION: a primer for amplification of the sequence of
      SEQ ID NO: 26

<400> SEQUENCE: 27

```
tctagaggat ccgctgcgta tcgttcgcgc catgc                                35
```

<210> SEQ ID NO 28
<211> LENGTH: 48
<212> TYPE: DNA
<213> ORGANISM: Artificial
<220> FEATURE:
<223> OTHER INFORMATION: a primer for amplification of the sequence of
      SEQ ID NO: 26

<400> SEQUENCE: 28

```
cgatcagcaa tgactgaccg gtcatggcgc cggtaacaag tgcgactt                  48
```

<210> SEQ ID NO 29
<211> LENGTH: 624
<212> TYPE: DNA
<213> ORGANISM: Artificial
<220> FEATURE:
<223> OTHER INFORMATION: a homologous region 2 of budC gene

<400> SEQUENCE: 29

```
aagtcgcact tgttaccggc gccatgaccg gtcagtcatt gctgatcgac ggcggcatgg     60
tgtttaacta ataaaaaaaa gctctgacat ggcttgcccc tgctttcgcg caggggcttt    120
ttttggtttg ggtgtaagtg taagcatccc ggagaaacga agcatcgata tttgagggct    180
tctggcgttc tcacttacgc ttcgacacga cgtgggcaat ctgactggga tgaaggtctg    240
atttgagcga ggagcggaag ttcgggaacg ggatagctct gacctgccac caggattaga    300
tacaaccgtc agttagtaag gtcggttttgt ttaccttcac attttccatt tcgccaccgt    360 gctgcaaaact ctgatggcgt ctgataattc agtgctgaat gtggacgaca ctcgttataa    420
tcctgccgcc agtcattaat gatttttcctt gcgtgaacga tatcgctgaa ccagtgctca    480
ttcaggcatt catcgcgaaa tcgtccgtta aagctctcaa taaatccgtt ctgcgttggc    540
ttgcccggct ggattaagcg caactcaaca ccatgctcaa aggcccattg atccagtgca    600
cggcaagtga actccggccc ctgg                                           624
```

<210> SEQ ID NO 30
<211> LENGTH: 48
<212> TYPE: DNA
<213> ORGANISM: Artificial
<220> FEATURE:
<223> OTHER INFORMATION: a primer for amplification of the sequence of
      SEQ ID NO: 29

<400> SEQUENCE: 30

```
aagtcgcact tgttaccggc gccatgaccg gtcagtcatt gctgatcg                  48
```

-continued

```
<210> SEQ ID NO 31
<211> LENGTH: 31
<212> TYPE: DNA
<213> ORGANISM: Artificial
<220> FEATURE:
<223> OTHER INFORMATION: a primer for amplification of the sequence of
      SEQ ID NO: 29

<400> SEQUENCE: 31
gcggccgccc aggggccgga gttcacttgc c                                      31

<210> SEQ ID NO 32
<211> LENGTH: 1216
<212> TYPE: DNA
<213> ORGANISM: Artificial
<220> FEATURE:
<223> OTHER INFORMATION: a DNA fragment in which the homologous regions
      1 and 2 of budC gene are ligated

<400> SEQUENCE: 32
gctgcgtatc gttcgcgcca tgcaggacat cgtcaacagc gacgtcacgt tgaccgtgga       60
catgggcagc ttccatatct ggattgcccg ctacctgtac agcttccgcg cccgccaggt      120
gatgatctcc aacggccagc agaccatggg cgtcgccctg ccctgggcca tcggcgcctg      180
gctggtcaat cctgagcgca aagtggtctc cgtctccggc gacggcggct tcctgcagtc      240
gagcatggag ctggagaccg ccgtccgcct gaaagccaac gtgctgcacc tgatctgggt      300
cgataacggc tacaacatgg tggccattca ggaagagaaa aataccagc gcctgtccgg       360 cgtcgagttt gggccgatgg atttaaagc ctatgccgaa tccttcggcg cgaaagggtt      420
tgccgtggaa agcgccgagg cgctggagcc gaccctgcgc gcggcgatgg acgtcgacgg      480
cccggcggta gtggccatcc cggtggatta tcgcgataac ccgctgctga tgggccagct      540
gcatctgagt cagattctgt aagtcatcac aataaggaaa gaaaaatgaa aaaagtcgca      600
cttgttaccg gcgccatgac cggtcagtca ttgctgatcg acggcggcat ggtgtttaac      660
taataaaaaa aagctctgac atggcttgcc cctgctttcg cgcaggggct ttttttggtt      720
tgggtgtaag tgtaagcatc ccggagaaac gaagcatcga tatttgaggg cttctggcgt      780
tctcacttac gcttcgacac gacgtgggca atctgactgg gatgaaggtc tgatttgagc      840
gaggagcgga agttcgggaa cgggatagct ctgacctgcc accaggatta gatacaaccg      900
tcagttagta aggtcggttt gtttaccttc acatttccca tttcgccacc gtgctgcaaa      960
ctctgatggc gtctgataat tcagtgctga atgtggacga cactcgttat aatcctgccg     1020
ccagtcatta atgattttcc ttgcgtgaac gatatcgctg aaccagtgct cattcaggca     1080
ttcatcgcga aatcgtccgt taaagctctc aataaatccg ttctgcgttg gcttgcccgg     1140
ctggattaag cgcaactcaa caccatgctc aaaggcccat tgatccagtg cacggcaagt     1200
gaactccggc ccctgg                                                    1216

<210> SEQ ID NO 33
<211> LENGTH: 4236
<212> TYPE: DNA
<213> ORGANISM: Klebsiella pneumoniae

<400> SEQUENCE: 33
gaacatcgcc agaaagcgtt tcaccgtacg cgagcgctcg aagcgccgcc aggcgatggc       60
gatatcggtc ttcagcggcg ccccgctaag cgggtgatag ctgacgttcg gctgctggat      120
gcaggtcatc gactgcggaa ccagcgcgaa gccgaagcca gcattgacca tgctcagcga      180
```

| | |
|---|---|
| cgacgaaatt tgcgacgact gccaggcgcg ctccatatcg atcccggcgc gcagacagct | 240 |
| gttgtacacc agctcataca gcccgggggc cacctcccgc gggaagagga tcggcgccac | 300 |
| gtcgcgcagc tgctccaggg ccagggtcgg ctgcgtcgcc agcgggttat cgcgcggcag | 360 |
| cgcgataacc atcggctcct catcgataat ccgcagatta aaggctttac tgctctcgca | 420 |
| cggcaggcgg acgaaggcga tatccagctc ggcctcgctc agggcggtca tcagattggc | 480 |
| catattgtct tccatctggt gcagggtcac cccggggtgg tcgagctgaa acggtgcag | 540 |
| cagcgtgaag atttgcggat ggaaagcatc agaactggta atgcctagcg acaggctgcc | 600 |
| gttcatcccg cgcgcaatgc ccttggcctt ctccagcgcc gcatcgctca tggcgaggat | 660 |
| ctggcgggca tcctcataga aagactctcc cgcttccgtc agctccaccc cgcgggttaa | 720 |
| acgccggaac agcggggtcc ccacctcgcg ctcaagccgc tgaatttgct gacttaacgg | 780 |
| aggctgtgaa atacccagct ccttggcggc ctgggtgaag tgccgcgtcc tggcgacggc | 840 |
| gacaaaatag cgaagataac gaagttccat atcgaaaacg tctcaaacca gcatggtttc | 900 |
| tatattggaa ctgtgagctg aatcgggtca acatttattt aacctttctt atatttgttg | 960 |
| aacgaggaag tggtatatga atcattctgc tgaatgcacc tgcgaagaga gtctatgcga | 1020 |
| aaccctgcgg gcgttttccg cgcagcatcc cgagagcgtg ctctatcaga catcgctcat | 1080 |
| gagcgccctg ctgagcgggg tttacgaagg cagcaccacc atcgccgacc tgctgaaaca | 1140 |
| cggcgatttc ggcctcggca cctttaatga gctggacggg gagctgatcg ccttcagcag | 1200 |
| tcaggtctat cagctgcgcg ccgacggcag cgcgcgcaaa gcccagccgg agcagaaaac | 1260 |
| gccgttcgcg gtgatgacct ggttccagcc gcagtaccgg aaaacctttg accatccggt | 1320 |
| gagccgccag cagctgcacg aggtgatcga ccagcaaatc ccctctgaca acctgttctg | 1380 |
| cgccctgcgc atcgacggcc atttccgcca tgcccatacc cgcaccgtgc gcgccagac | 1440 |
| gccgccgtac cggcgatga ccgacgtact cgacgatcag ccggtgttcc gctttaacca | 1500 |
| gcgcgaaggg gtgctggtcg gcttccggac ccccgcagcat atgcagggga tcaacgtcgc | 1560 |
| cgggtatcac gagcatttta ttaccgatga ccgcaaaggc ggcggtcacc tgctggatta | 1620 |
| ccagctcgac cacggggtgc tgaccttcgg cgaaattcac aagctgatga tcgacctgcc | 1680 |
| cgccgacagc gcgttcctgc aggctaatct gcatcccgat aatctcgatg ccgccatccg | 1740 |
| ttccgtagaa agttaagggg gtcacatgga caaacagtat ccggtacgcc agtgggcgca | 1800 |
| cggcgccgat ctcgtcgtca gtcagctgga agcacagggg gtacgccagg tgttcggcat | 1860 |
| ccccggcgca aaaatcgaca aggtcttcga ttcactgctg gattcctcca ttcgcattat | 1920 |
| tccggtacgc cacgaagcca acgccgcatt tatggccgcc gccgtcggac gtattaccgg | 1980 |
| caaagcgggc gtggcgctgg tcacctccgg tccgggttgt tctaacctga tcaccggcat | 2040 |
| ggccaccgcg aacagcgaag cgacccggt ggtggccctg gcggcgcgg taaaacgcgc | 2100 |
| cgataaagcc aaacaggtcc accagagtat ggatacggtg gcgatgttca gcccggtcac | 2160 |
| caaatacgcg gtcgaggtga cggcgccgga tgcgctggcg gaagtggtct ccaacgcctt | 2220 |
| ccgcgccgcc gagcagggcc ggccgggcag cgcgttcgtt agcctgccgc aggatgtggt | 2280 |
| cgatggcccg gtcagcggca agtactgcc ggccagcggg gccccgcaga tgggcgccgc | 2340 |
| gccggatgat gccatcgacc aggtggcgaa gcttatcgcc caggcgaaga acccgatctt | 2400 |
| cctgctcggc ctgatggcca gccagccgga aaacagcaag gcgctgcgcc gtttgctgga | 2460 |
| gaccagccat attccagtca ccagcaccta tcaggccgcc ggagcggtga atcaggataa | 2520 |
| cttctctcgc ttcgccggcc gggttgggct gtttaacaac caggccgggg accgtctgct | 2580 |

```
gcagcttgcc gacctggtga tctgcatcgg ctacagcccg gtggaatacg aaccggcgat    2640
gtggaacagc ggcaacgcga cgctggtgca catcgacgtg ctgcccgcct atgaagagcg    2700
caactacacc ccggatgtcg agctggtagg cgatatcgcc ggcactctca acaagctggc    2760
gcaaaatatc gatcatcggc tggtgctctc cccgcaggca gcggagatcc tccgcgaccg    2820
ccagcaccag cgcgagctgc tggaccgccg cggcgcgcag ctcaaccagt ttgccctgca    2880
tccgctgcgt atcgttcgcg ccatgcagga catcgtcaac agcgacgtca cgttgaccgt    2940
ggacatgggc agcttccata tctggattgc ccgctacctg tacagcttcc gcgcccgcca    3000
ggtgatgatc tccaacggcc agcagaccat gggcgtcgcc ctgccctggg ccatcggcgc    3060
ctggctggtc aatcctgagc gcaaagtggt ctccgtctcc ggcgacggcg gcttcctgca    3120
gtcgagcatg gagctggaga ccgccgtccg cctgaaagcc aacgtgctgc acctgatctg    3180
ggtcgataac ggctacaaca tggtggccat tcaggaagag aaaaaatacc agcgcctgtc    3240
cggcgtcgag tttgggccga tggattttaa agcctatgcc gaatccttcg gcgcgaaagg    3300
gtttgccgtg gaaagcgccg aggcgctgga gccgaccctg cgcgcggcga tggacgtcga    3360
cggcccggcg gtagtggcca tcccggtgga ttatcgcgat aacccgctgc tgatgggcca    3420
gctgcatctg agtcagattc tgtaagtcat cacaataagg aaagaaaaat gaaaaagtc    3480 gcacttgtta ccggcgccgg ccaggggatt ggtaaagcta tcgcccttcg tctggtgaag    3540
gatggatttg ccgtggccat tgccgattat aacgacgcca ccgccaaagc ggtcgcctcc    3600
gaaatcaacc aggccggcgg ccgcgccatg gcggtgaaag tggatgtttc tgaccgcgac    3660
caggtatttg ccgccgtcga acaggcgcgc aaaacgctgg gcggcttcga cgtcatcgtc    3720
aacaacgccg gcgtggcgcc atccacgccg atcgagtcca ttaccccgga gattgtcgac    3780
aaagtctaca acatcaacgt caaaggggtg atctgggca tccaggcagc ggtcgaggcc    3840
tttaagaaag agggtcacgg cgggaaaatc atcaacgcct gttcccaggc cggccacgtc    3900
ggcaacccgg agctggcggt atatagctcg agtaaattcg cggtacgcgg cttaacccag    3960
accgccgctc gcgacctcgc gccgctgggc atcacggtca acggctactg cccgggggatt    4020 gtcaaaacgc cgatgtgggc cgaaattgac cgccaggtgt ccgaagccgc cggtaaaccg    4080
ctgggctacg gtaccgccga gttcgccaaa cgcatcaccc tcggccgcct gtccgagccg    4140
gaagatgtcg ccgcctgcgt ctcctatctt gccagcccgg attctgatta tatgaccggt    4200
cagtcattgc tgatcgacgg cggcatggtg tttaac                              4236
```

<210> SEQ ID NO 34
<211> LENGTH: 701
<212> TYPE: DNA
<213> ORGANISM: Artificial
<220> FEATURE:
<223> OTHER INFORMATION: a homologous region 1 of budRABC gene

<400> SEQUENCE: 34

```
ccagctggtg ctcaatggct tcggcgacag cagccacgcc cgggctgaag tcgccgcgct      60
gggcaagatc cccggctatc acgacgccga cctgcgcgac gtcgggcaga tcgaggcgat    120
gatgcgctat gccgaaagca ccttcggcgg cgtcgatatc gtgatcaata cgccggcat    180 ccagcacgtg gccccggtgg agcagttccc ggtggacaaa tggaacgata ttctcgccat    240
caatctctcc agcgtcttcc acaccacccg cctggcgctg ccgggtatgc gccagcgcaa    300
ctgggggcgc atcatcaaca ttgcctcagt gcatggcctg gtggcgtcga agagaaatc    360
```

```
ggcctacgtc gccgccaagc acgcggtggt cgggctgacc aaaaccgtgg ccctggaaac    420
cgcgcgcagc ggtatcacct gcaacgccat ctgccctggc tgggtgctaa ccccgctggt    480
gcagcagcag atcgacaaac gcatcgccga ggggtcgac ccggagcagg ccagcgccca     540
gctgctggcg aaaaacagc cctccgggga gtttgtcacc ccgcagcagc tgggcgaaat     600
ggcgctgttt ctgtgcagcg atgccgccgc ccaggtgcgc ggcgccgcat ggaacatgga    660
tggcggctgg gtggcgcagt aagccgctgg cgccgcgaag a                       701
```

<210> SEQ ID NO 35
<211> LENGTH: 33
<212> TYPE: DNA
<213> ORGANISM: Artificial
<220> FEATURE:
<223> OTHER INFORMATION: a primer for amplification of the sequence of SEQ ID NO: 34

<400> SEQUENCE: 35

```
tagaggatcc ccagctggtg ctcaatggct tcg                                 33
```

<210> SEQ ID NO 36
<211> LENGTH: 44
<212> TYPE: DNA
<213> ORGANISM: Artificial
<220> FEATURE:
<223> OTHER INFORMATION: a primer for amplification of the sequence of SEQ ID NO: 34

<400> SEQUENCE: 36

```
caagccatgt cagagctttt ttttatcttc gcggcgccag cggc                     44
```

<210> SEQ ID NO 37
<211> LENGTH: 701
<212> TYPE: DNA
<213> ORGANISM: Artificial
<220> FEATURE:
<223> OTHER INFORMATION: a homologous region 2 of budRABC gene

<400> SEQUENCE: 37

```
taaaaaaaag ctctgacatg gcttgcccct gctttcgcgc aggggctttt tttggtttgg    60
gtgtaagtgt aagcatcccg gagaaacgaa gcatcgatat ttgagggctt ctggcgttct    120
cacttacgct tcgacacgac gtgggcaatc tgactgggat gaaggtctga tttgagcgag    180
gagcggaagt tcgggaacgg gatagctctg acctgccacc aggattagat acaaccgtca    240
gttagtaagg tcggtttgtt taccttcaca ttttccattt cgccaccgtg ctgcaaactc    300
tgatggcgtc tgataattca gtgctgaatg tggacgacac tcgttataat cctgccgcca    360
gtcattaatg attttccttg cgtgaacgat atcgctgaac cagtgctcat tcaggcattc    420
atcgcgaaat cgtccgttaa agctctcaat aaatccgttc tgcgttggct tgcccggctg    480
gattaagcgc aactcaacac catgctcaaa ggcccattga tccagtgcac ggcaagtgaa    540
ctccggcccc tggtcagttc ttatcgtcgc cggatagcct cgaaacagtg caatgctgtc    600
cagaatacgc gagacctgaa cgcctgaaat cccaaaggca acagtgaccg tcaggcattc    660
ctttgtgaaa tcatcgacgc aggtaagaca cttgatcctg c                       701
```

<210> SEQ ID NO 38
<211> LENGTH: 44
<212> TYPE: DNA
<213> ORGANISM: Artificial
<220> FEATURE:
<223> OTHER INFORMATION: a primer for amplification of the sequence of

SEQ ID NO: 37

<400> SEQUENCE: 38
gccgctggcg ccgcgaagat aaaaaaaagc tctgacatgg cttg      44

<210> SEQ ID NO 39
<211> LENGTH: 36
<212> TYPE: DNA
<213> ORGANISM: Artificial
<220> FEATURE:
<223> OTHER INFORMATION: a primer for amplification of the sequence of
      SEQ ID NO: 37

<400> SEQUENCE: 39
gatcgcggcc gcgcaggatc aagtgtctta cctgcg      36

<210> SEQ ID NO 40
<211> LENGTH: 1402
<212> TYPE: DNA
<213> ORGANISM: Artificial
<220> FEATURE:
<223> OTHER INFORMATION: a DNA fragment in which the homologous regions
      1 and 2 of budRABC gene are ligated

<400> SEQUENCE: 40

| | |
|---|---|
| ccagctggtg ctcaatggct tcggcgacag cagccacgcc cgggctgaag tcgccgcgct | 60 |
| gggcaagatc cccggctatc acgacgccga cctgcgcgac gtcgggcaga tcgaggcgat | 120 |
| gatgcgctat gccgaaagca ccttcggcgg cgtcgatatc gtgatcaata acgccggcat | 180 |
| ccagcacgtg gccccggtgg agcagttccc ggtggacaaa tggaacgata ttctcgccat | 240 |
| caatctctcc agcgtcttcc acaccacccg cctggcgctg ccgggtatgc gccagcgcaa | 300 |
| ctgggggcgc atcatcaaca ttgcctcagt gcatggcctg gtggcgtcga agagaaatc | 360 |
| ggcctacgtc gccgccaagc acgcggtggt cgggctgacc aaaaccgtgg ccctggaaac | 420 |
| cgcgcgcagc ggtatcaccct gcaacgccat ctgccctggc tgggtgctaa ccccgctggt | 480 |
| gcagcagcag atcgacaaac gcatcgccga ggggtcgac ccggagcagg ccagcgccca | 540 |
| gctgctggcg gaaaaacagc cctccgggga gtttgtcacc ccgcagcagc tgggcgaaat | 600 |
| ggcgctgttt ctgtgcagcg atgccgccgc ccaggtgcgc ggcgccgcat ggaacatgga | 660 |
| tggcggctgg gtggcgcagt aagccgctgg cgccgcgaag ataaaaaaaa gctctgacat | 720 |
| ggcttgcccc tgcttttcgcg caggggcttt ttttggtttg ggtgtaagtg taagcatccc | 780 |
| ggagaaacga agcatcgata tttgagggct tctggcgttc tcacttacgc ttcgacacga | 840 |
| cgtgggcaat ctgactggga tgaaggtctg atttgagcga ggagcggaag ttcgggaacg | 900 |
| ggatagctct gacctgccac caggattaga tacaaccgtc agttagtaag gtcggtttgt | 960 |
| ttaccttcac attttccatt tcgccaccgt gctgcaaact ctgatggcgt ctgataattc | 1020 |
| agtgctgaat gtggacgaca ctcgttataa tcctgccgcc agtcattaat gatttccctt | 1080 |
| gcgtgaacga tatcgctgaa ccagtgctca ttcaggcatt catcgcgaaa tcgtccgtta | 1140 |
| aagctctcaa taaatccgtt ctgcgttggc ttgcccggct ggattaagcg caactcaaca | 1200 |
| ccatgctcaa aggcccattg atccagtgca cggcaagtga actccggccc ctggtcagtt | 1260 |
| cttatcgtcg ccggatagcc tcgaaacagt gcaatgctgt ccagaatacg cgagacctga | 1320 |
| acgcctgaaa tcccaaaggc aacagtgacc gtcaggcatt cctttgtgaa atcatcgacg | 1380 |
| caggtaagac acttgatcct gc | 1402 |